(12) United States Patent
Asaoka et al.

(10) Patent No.: US 7,966,165 B2
(45) Date of Patent: Jun. 21, 2011

(54) SOIL-WATER COUPLED ANALYZER AND SOIL-WATER COUPLED ANALYSIS METHOD

(75) Inventors: Akira Asaoka, Kyoto (JP); Toshihiro Noda, Nagoya (JP); Masaki Nakano, Nagoya (JP)

(73) Assignee: National University Corporation Nagoya University, Nagoya (JP)

( * ) Notice: Subject to any disclaimer, the term of this patent is extended or adjusted under 35 U.S.C. 154(b) by 551 days.

(21) Appl. No.: 12/083,302

(22) PCT Filed: Aug. 1, 2006

(86) PCT No.: PCT/JP2006/315198
§ 371 (c)(1),
(2), (4) Date: Apr. 9, 2008

(87) PCT Pub. No.: WO2007/046178
PCT Pub. Date: Apr. 26, 2007

(65) Prior Publication Data
US 2009/0164179 A1    Jun. 25, 2009

(30) Foreign Application Priority Data
Oct. 17, 2005  (JP) .............................. 2005-301415

(51) Int. Cl.
G06F 9/455 (2006.01)
(52) U.S. Cl. ........................................... 703/10
(58) Field of Classification Search ............. 703/6, 10; 73/73, 649; 702/6, 22, 32; 405/129.2; 210/632; 429/24
See application file for complete search history.

(56) References Cited

U.S. PATENT DOCUMENTS

| 4,176,058 | A | * | 11/1979 | Grobler .................... 210/632 |
| 6,234,008 | B1 | * | 5/2001 | Sjoblom et al. ............ 73/73 |
| 6,694,815 | B2 | | 2/2004 | Kazama et al. |

(Continued)

FOREIGN PATENT DOCUMENTS
JP    A-2003-278171    10/2003

OTHER PUBLICATIONS

McFadden et al., "The vsicular layer and carbonte collars of desert soil and pavement: formation and relation to climate change", 1997.*

(Continued)

*Primary Examiner* — Kandasamy Thangavelu
(74) *Attorney, Agent, or Firm* — Oliff & Berridge, PLC

(57) ABSTRACT

The soil-water coupled analysis program of the invention computes a global L matrix and a modified global L matrix regarding a volume change rate of a soil skeleton over time, a global H matrix regarding a water permeability of soil, a global M matrix regarding a mass, and a global K matrix regarding a tangent stiffness of the soil skeleton, based on input settings of soils, such as clay, intermediate soil, and sand, to respective elements of a soil foundation, input settings of a solid soil model, and input settings of analysis conditions (steps S140 to S165). The soil-water coupled analysis program formulates a global tangent stiffness equation (simultaneous linear equations) using all these computed matrixes and determines an unknown 'jerk field' and a 'pore water pressure field' under given boundary conditions, for example, a given deformation condition and a given stress rate condition (step S170). This enables highly-accurate dynamic and static analyses in soil foundations of various soils from sand to intermediate soils and clay.

12 Claims, 13 Drawing Sheets

U.S. PATENT DOCUMENTS

| | | | |
|---|---|---|---|
| 6,937,939 B1* | 8/2005 | Shibusawa et al. | 702/22 |
| 7,003,405 B1* | 2/2006 | Ho | 702/32 |
| 2003/0177834 A1* | 9/2003 | Kazama et al. | 73/649 |
| 2006/0029473 A1* | 2/2006 | Khire | 405/129.2 |
| 2006/0069510 A1* | 3/2006 | Hauge | 702/6 |

OTHER PUBLICATIONS

Braunet al., "Comparison of soil hydraulic parametrizations for Mesoscale meteorological models", 2005.*

Vogel et al., "Porous media with linearly variable hydraulic properties", 1991.*

Manoliadis, O.G., "A dynamic soil water model for environmental simulation problems", 2000.*

Chen et al.; "Dynamic Large Deflection Analysis of Structures by a Combined Finite Element-Riccati Transfer Matrix Method On a Microcomputer;" *Computers & Structures*; vol. 39; No. 6; pp. 699-703; 1991.

"GeoFEM, Multi-Purpose/Multi-Physics Parallel Finite Element Simulator/Platform for Solid Earth;" Coastal Development Institute of Technology, www.ysk.nilim.go.jp/geofem/phgeo01j.html; May 13, 2005.

* cited by examiner

FIG. 3

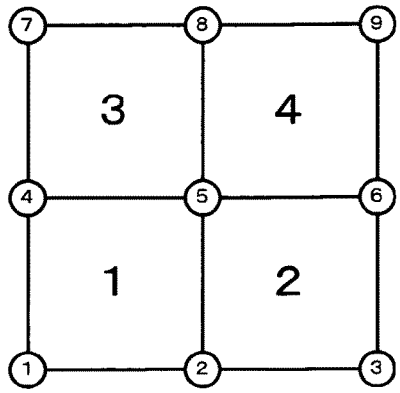

FIG. 4

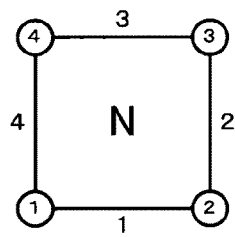

FIG. 5

```
1   ! JCOND Computation condition: plane strain (1), axisymmettric (3), three-dimensional (5)
1   ! JDEF  Deformation theory: small deformation (0), finite deformation (1)
2   ! IRATE Effective stress rate in finite deformation theory: Cauchy-Jaumann(1), Green-Nagdhi(2)
1   ! ICON  Convergence: Yes (1), No (0)
23  ! ISLMDL Constitutive equation: original Cam-clay model with super-subloading yield surfaces and rotational
           hardening (3), modified Cam-clay model with super-subloading yield surfaces and rotational hardening (23)
0   ! ielorga State quantity output data, element average of Gauss points (0), Gauss point (1-4)
0   ! JBINRY Output data format: Text (0), Binary (1)
0   ! jgrav  Consideration of self weight: No (specimen) (0), Yes (soil foundation) (1)
```

FIG. 6

| | |
|---|---|
| 1 | !current program number (NPRO) |
| 2000 | !number of computation steps |
| 1.0d0 | !computation time DT (sec/step) |
| 1.0D0 | !number of divisions of drilling load (REMO) in excavation |
| 1.0D0 | !number of divisions of distributed load (remt) in application of distributed load |
| D:¥indat¥soil¥test.dat | !input file for soil material parameters and initial values |
| D:¥indat¥mesh¥test.dat | !input file for mesh data |
| D:¥outdat¥test¥file20¥npro001.dat | !specification of output file for initial computation conditions used in next NPRO |
| D:¥outdat¥test¥file31¥npro001.dat | !specification of output file for coordinates (ZHI) |
| D:¥outdat¥test¥file311¥npro001.dat | !specification of output file for state classification (unloading, loading (plastic compression/expansion, hardening/softening)) |
| D:¥outdat¥test¥file32¥npro001.dat | !specification of output file for reactive force (Bts) |
| D:¥outdat¥test¥file34¥npro001.dat | !Specification of output file for excess pore water pressure |
| D:¥outdat¥test¥file36¥npro001.dat | !specification of output file for mean effective stress p' and shear stress q |
| D:¥outdat¥test¥file37¥npro001.dat | !specification of output file for degree R of overconsolidation (1/OCR) |
| D:¥outdat¥test¥file38¥npro001.dat | !specification of output file for degree R* of structure (1/STR) |
| D:¥outdat¥test¥file39¥npro001.dat | !specification of output file for slope (Ms) of hardening /softening threshold |
| D:¥outdat¥test¥file40¥npro001.dat | !specification of output file for plastic volume strain |
| D:¥outdat¥test¥file55¥npro001.dat | !specification of output file for initial conditions |
| D:¥outdat¥test¥file74¥npro001.dat | !specification of output file for slope (Ma) of plastic compression/expansion threshold line |
| D:¥outdat¥test¥file75¥npro001.dat | !specification of output file for evolution degree of anisotropy (Iβ I/mb) |
| D:¥outdat¥test¥file83¥npro001.dat | !specification of putput file for elapsed time |
| D:¥outdat¥test¥file90¥npro001.dat | !output of file***.dat (preceding output file specifications) |

FIG. 7

| | | |
|---|---|---|
| 1   0 | | !number of soil types, number of elastic body types |
| 0 | irev [DP]:0, [DSP]:2 [T·DP]:3 | !specification of plastic measure adopted in evolution law of structure |
| 2.50000 | CNYU | !intercept N of isotropic normal consolidation line of remolded soil |
| 1.20 | CMYU | !critical state constant M |
| 0.130 | RAMDA | !compression index $\lambda$ |
| 0.010 | KAPPA | !swelling index $\kappa$ |
| 0.30 | POI | !Poisson's ratio $\nu$ |
| 1.00d-3 | PK | !coefficient of permeability k |
| 2.68 | RS | !specific gravity Gs of soil particles |
| 1.0 | KI:0.9999 | !initial lateral pressure coefficient K0 |
| 5.00 | OCR | !initial degree R0 of overconsolidation |
| 10.00 | STR | !initial degree R*0 of structure |
| 0.05 | COSUB | !normal consolidation index m |
| 8 | NKS  (U*), m*:7,abc:8 | !U* shape |
| 0.30 | COSUP:a,m* | !structural degradation index a |
| 1.00 | COSUPb:b | !structural degradation index b |
| 1.00 | COSUP2c:c | !structural degradation index c |
| 0.0 | BR | !rotational hardening index br |
| 1.0 | CMB | !rotational hardening limit surface mb |
| 1.0 | bk0 | !initial degree of anisotropy |
| 1.0 | EEM | !initial void ratio |
| #———————— | | |
| #———————— | | |
| 5.0 | HS | !height of soil foundation/specimen |
| 5.0 | HW | !water surface level |
| 1.0 | PDEL | !initial overburden pressure on the surface of soil foundation |
| 3.0 | PC | !initial consolidation pressure of specimen |
| 0.0 | CONSTP | !cell pressure (tensile: positive) |
| #———— unit ———— | | |
| 1  1  1 | | !settings of unit system (time, force, and length) |

FIG. 8

```
4  9  2  4  1  0 --------------- number of elements, number of nodes, number of elements with application of distributed load rate,
                                  number of nodes per element, number of computation steps, number of elastic elements
1  -1  0.00000  -1  0.00000 ⎤
2  -1  0.00000  -1  0.00000 ⎥
3  -1  0.00000  -1  0.00000 ⎥    node number, type of (boundary) condition in x-direction, its value, type of (boundary) condition in y-
4  -1  0.00000   1  0.00000 ⎥    direction, its value
5   1  0.00000   1  0.00000 ⎬     type of (boundary) condition:
6  -1  0.00000   1  0.00000 ⎥       0: coordinate control, 1: load rate control,
7  -1  0.00000   1  0.00000 ⎥      -1:displacement rate control, -2:displacement acceleration control
8  -1  0.00000   1  0.00000 ⎥
9  -1  0.00000   1  0.00000 ⎦

1  2  5  4 ⎤
2  2  3  6  5 ⎬ element number, mapping of local node number to global node number
3  4  5  8  7 ⎥
4  5  6  9  8 ⎦

1  0.00000  0.00000 ⎤
2  1.25000  0.00000 ⎥
3  2.50000  0.00000 ⎥
4  0.00000  2.50000 ⎥
5  1.25000  2.50000 ⎬ node number, coordinate in x-direction, coordinate in y-direction
6  2.50000  2.50000 ⎥
7  0.00000  5.00000 ⎥
8  1.25000  5.00000 ⎥
9  2.50000  5.00000 ⎦

3 ------------- number of nodes requiring output of reactive force
14  16  18 --- corresponding node numbers including directions (example: y direction of node 7: 7*2=14)

2  2  0.00000  0.00000  0.00000  0.00000 ⎫ elements with application of distributed load rate, side of application
4  2  0.00000  0.00000  0.00000  0.00000 ⎬  values of distributed load rate of its left node in x-direction and y-direction
                                           ⎭  values of distributed load rate of its right node in x-direction and y-direction 1  2  2  3  1  1 ⎤ element number, specification of (four) relevant elements, soil type
2  2  4  1  1 ⎬   relevant element having identical number with element number: undrained condition
3  2  1  3  3  1 ⎥ relevant element having minus number: drained condition
4  2  4  4  3 ⎦

0 ------------- number of conditions satisfying fixed length between two nodes
0 ------------- number of conditions satisfying fixed length angle between three nodes
1 ------------- condition number satisfying fixed angle, specification of nodes involved in the condition
7  8  9  1       number of conditions satisfying fixed direction of relative velocity of two nodes specified by relative position vectors of former nodes and latter nodes
1 ------------- nodes specified by relative position vectors of former two nodes and latter two nodes, specification of nodes involved in the condition
8  7  4          number of conditions satisfying equal displacement (velocity)
0

1 ------------- number of regular waves input into model, number of irregular waves input into model
1  -2.549291  6.283184 -------- type of regular wave variation, number of nodes under influence of regular wave vibration, amplitude, period
14 ------------- corresponding node numbers including directions (example: y direction of node 7: 7*2=14)
```

FIG. 12

```
4  9  2  4  18   8  200  200   2  4  0
         number of elements, number of nodes, number of elements with application of distributed load rate, number of nodes per element,
         number of nodes per element × number of dimensions, number of nodes per element × number of dimensions, specified number of computation steps,
         total number of implemented computation steps, number of dimensions, number of Gauss points per element, number of elastic elements
1   1   23   0   0   0
         analysis condition, deformation theory, effective stress rate in adoption of finite deformation theory, convergence or non-convergence, constitutive equation,
         output method of state quantity data, format of output data, consideration or non-consideration of self weight (see input file)

1  -1  0.000000000000000E+00  -1  0.000000000000000E+00
2   1  0.000000000000000E+00  -1  0.000000000000000E+00
3   1  0.000000000000000E+00  -1  0.000000000000000E+00
4  -1  0.000000000000000E+00   1  0.000000000000000E+00
5   1  0.000000000000000E+00   1  0.000000000000000E+00      node number, type of (boundary) condition in x-direction, its value,
6   1  0.000000000000000E+00   1  0.000000000000000E+00      type of (boundary) condition in y-direction, its value, type of (boundary) condition
7  -1  0.000000000000000E+00   1  0.000000000000000E+00
8  -1  0.000000000000000E+00   1  0.000000000000000E+00
9  -1  0.000000000000000E+00   1  0.000000000000000E+00

3                      number of nodes requiring output of reactive force
14  16  18            corresponding node numbers including directions (example: y direction of node 7: 7*2=14)

(omission) material parameters of respective Gauss points in each element, values of components at each node, value of pore water
pressure in each element, values of effective stress components of respective Gauss points in each element, degree of structure, …, etc.

1  1  2  3  1  2  2  2  4  1  3  1  4  3  3  4  2  4  4  3
         sequence of element number and specified (four) relevant elements with regard to four elements 0                      number of conditions satisfying fixed length between two nodes
1                      number of conditions satisfying fixed angle between three nodes
1   7  8  9  1         condition number satisfying fixed angle, specification of nodes involved in the condition
                       number of conditions satisfying fixed direction of relative velocity of two nodes specified by relative position vectors of former two nodes and latter two nodes
1   8  7  4            condition number satisfying fixed direction, specification of nodes involved in the condition
0                      number of conditions satisfying equal displacement (velocity)

1  1  1  1             type of soil element 1                      number of input of regular waves, number of input of irregular waves
0
1  -2.549291  6.283184  type of regular wave vibration, number of nodes under influence of regular wave vibration, amplitude, period
14                     corresponding node number including directions (example: y direction of node 7: 7*2=14)

0.200000000000000E-03   total time since start of computation
```

SOIL-WATER COUPLED ANALYZER AND SOIL-WATER COUPLED ANALYSIS METHOD

TECHNICAL FIELD

The present invention relates to a soil-water coupled analyzer and a corresponding soil-water coupled analysis method. More specifically the invention pertains to the soil-water coupled analyzer and the corresponding soil-water coupled analysis method of performing deformation analysis of a soil skeleton.

BACKGROUND ART

One proposed soil skeleton analysis program is designed to enable three-dimensional soil deformation analysis or three-dimensional consolidation analysis (see, for example, Non-Patent Reference 1). Another proposed soil skeleton analysis program uses a mechanical constitutive model expressing static behaviors of a soil foundation (see, for example, Non-Patent Reference 2). These soil skeleton analysis programs are expected to accurately estimate the water permeability, the consolidation, the stress in the soil foundation, the shear, the earth pressure, and the slope stability.
Non-Patent Reference 1: brochure of 'FEM analysis support system of soil structures AFIMEX-GT', Fujitsu FIP Corporation, No. 0040708-2
Non-Patent Reference 2: homepage of 'GeoFEM, Multi-Purpose/Multi-Physics Parallel Finite Element Simulator/Platform for Solid Earth', Coastal Development Institute of Technology, searched on May 13, 2005.

DISCLOSURE OF THE INVENTION

The prior art soil skeleton analysis program is exclusively used for one soil type, for example, clay or sand, and does not allow accurate analysis with regard to intermediate soils as sand and clay mixtures generally found in reclaimed artificial soil foundations. The natural soil foundation is not made of sand alone or clay alone of an identical particle size but includes various types of soils, such as sand-rich clay and clay-mixed sand. The results of analysis according to the soil skeleton analysis program developed exclusively for sand or according to the soil skeleton analysis program developed exclusively for clay are thus significantly different from the actual behaviors of the soil foundation. The prior art soil skeleton analysis programs are not applicable to a layered soil foundation of sand and clay.

Rapid repeated loadings in uncompressed and undrained conditions cause liquefaction of a loose sand foundation, while relatively slow repeated loadings in a drained condition cause compaction of the sand foundation. The prior art soil skeleton analysis programs are applicable to analyze the liquefaction but are not applicable to analyze the compaction. Namely these analysis programs are usable only exclusively for analysis of the liquefaction. The prior art soil skeleton analysis program is executable only after identification of a target soil foundation as a sand foundation or a clay foundation suitable for the program with other indexes. The prior art analysis program is designed exclusively for dynamic analysis or for static analysis and is not applicable to static analysis following dynamic analysis as in the case of liquefaction-induced settlement.

In the soil-water coupled analyzer and the corresponding soil-water coupled analysis method, there is a demand of enabling both static and dynamic analyses of a soil skeleton. Accurate deformation analysis of the soil skeleton is demanded in soil foundations of various intermediate soils between sand and clay, as well as in layered soil foundations of clay, sand, and intermediate soil. Another need is iterative deformation analyses of the soil skeleton according to the soil conditions and the loading conditions. There is another demand of enabling static deformation analysis following dynamic deformation analysis, as well as dynamic deformation analysis following static deformation analysis.

At least part of the above and the other related demands is attained by a soil-water coupled analyzer and a corresponding soil-water coupled analysis method of the invention having the configurations discussed below.

According to one aspect, the present invention is directed to a soil-water coupled analyzer including: a data input unit that inputs data on conditions of a soil skeleton and data on external forces; and an analysis module that performs deformation analysis of the soil skeleton. The deformation analysis formulates simultaneous motion equations of rate type with respect to a pore water pressure and a velocity of the soil skeleton including a jerk term of the soil skeleton, based on the input data on the conditions of the soil skeleton and the input data on the external forces, and integrates the formulated simultaneous motion equations as needed under a given geometric boundary condition with regard to any of a displacement, a displacement rate, and an acceleration, a given mechanical boundary condition with regard to either of a stress and a stress rate, and given hydraulic boundary conditions with regard to either of the pore water pressure and a total water head and a flow of pore water, so as to obtain time history responses of a velocity field and a pore water pressure filed.

The soil-water coupled analyzer according to one aspect of the invention integrates the simultaneous motion equations of rate type with respect to the pore water pressure and the velocity of the soil skeleton including the jerk term of the soil skeleton as needed under the given geometric boundary condition with regard to any of the displacement, the displacement rate, and the acceleration, the given mechanical boundary condition with regard to either of the stress and the stress rate, and the given hydraulic boundary conditions with regard to either of the pore water pressure and the total water head and the flow of pore water, in order to obtain the time history responses of the velocity field and the pore water pressure filed. In the significant influence of the acceleration, the deformation analysis of the soil skeleton is performed by dynamic computations. In the little influence of the acceleration, on the other hand, the deformation analysis of the soil skeleton is performed by static computations. The soil-water coupled analyzer of this aspect thus enables both dynamic and static deformation analyses of the soil skeleton.

In one preferable application of the soil-water coupled analyzer of the invention, the analysis module calculates multiple terms based on the input data on the conditions of the soil skeleton and the input data on the external forces and formulates the simultaneous motion equations of rate type using the multiple calculated terms. The multiple terms include at least one of a first term regarding a volume change rate of the soil skeleton over time, a second term regarding a water permeability of soil, a third term regarding a mass, and a fourth term regarding a tangent stiffness of the soil skeleton. In this application, the analysis module may formulate the simultaneous motion equations of rate type using all of the first term, the second term, the third term, and the fourth term. This arrangement ensures appropriate deformation analysis of the soil skeleton.

In another preferable application of the soil-water coupled analyzer of the invention, the analysis module adopts a numerical analysis technique, such as a finite element method or a difference method, to formulate the simultaneous motion equations of rate type. This arrangement desirably facilitates the computations.

In the soil-water coupled analyzer of the invention, one example of the data on the conditions of the soil skeleton includes data on properties of multiple elements constituting the soil skeleton and data on relations between adjacent elements. The data on the properties of the multiple elements may include data on properties of soils. The settings are enabled for the properties of the respective multiple elements constituting the soil skeleton as well as for the relation between each pair of adjacent elements. Such setting enables accurate deformation analysis of the soil skeleton in the soil foundations including various intermediate soils between sand and clay and accurate deformation analysis of the soil skeleton in the layered soil foundations of clay, sand, and intermediate soils.

In the soil-water coupled analyzer of the invention, one example of the data on the external forces includes data on a load and a displacement applied to a soil-water coupled system. Another example of the data on the external forces includes data on a vibration applied to a soil-water coupled system. Such setting enables deformation analysis of the soil skeleton with regard to the load and the displacement or deformation analysis of the soil skeleton with regard to the vibration.

In one preferable application of the soil-water coupled analyzer of the invention, the analysis module performs the deformation analysis plural times with changing the data on the external forces. In this application, it is preferable that the analysis module performs the deformation analysis plural times with setting a result of a current cycle of the analysis prior to the change of the data on the external forces to an initial state of the data on the conditions of the soil skeleton for a next cycle of the analysis. This arrangement enables iterative deformation analyses of the soil skeleton according to the soil conditions and the loading conditions. This arrangement also enables static deformation analysis following dynamic deformation analysis, as well as dynamic deformation analysis following static deformation analysis.

According to another aspect, the invention is also directed to a soil-water coupled analysis method that performs deformation analysis of a soil skeleton. The deformation analysis formulates simultaneous motion equations of rate type with respect to a pore water pressure and a velocity of the soil skeleton including a jerk term of the soil skeleton, based on data on conditions of the soil skeleton and data on external forces, and integrates the formulated simultaneous motion equations as needed under a given geometric boundary condition with regard to any of a displacement, a displacement rate, and an acceleration, a given mechanical boundary condition with regard to either of a stress and a stress rate, and given hydraulic boundary conditions with regard to either of the pore water pressure and a total water head and a flow of pore water, so as to obtain time history responses of a velocity field and a pore water pressure filed.

The soil-water coupled analysis method according to another aspect of the invention integrates the simultaneous motion equations of rate type with respect to the pore water pressure and the velocity of the soil skeleton including the jerk term of the soil skeleton as needed under the given geometric boundary condition with regard to any of the displacement, the displacement rate, and the acceleration, the given mechanical boundary condition with regard to either of the stress and the stress rate, and the given hydraulic boundary conditions with regard to either of the pore water pressure and the total water head and the flow of pore water, in order to obtain the time history responses of the velocity field and the pore water pressure filed. In the significant influence of the acceleration, the deformation analysis of the soil skeleton is performed by dynamic computations. In the little influence of the acceleration, on the other hand, the deformation analysis of the soil skeleton is performed by static computations. The soil-water coupled analysis method of this aspect thus enables both dynamic and static deformation analyses of the soil skeleton.

In one preferable application of this aspect of the invention, the soil-water coupled analysis method calculates multiple terms based on the data on the conditions of the soil skeleton and the data on the external forces and formulates the simultaneous motion equations of rate type using the multiple calculated terms. The multiple terms include at least one of a first term regarding a volume change rate of the soil skeleton over time, a second term regarding a water permeability of soil, a third term regarding a mass, and a fourth term regarding a tangent stiffness of the soil skeleton. In this application, the soil-water coupled analysis method may formulate the simultaneous motion equations of rate type using all of the first term, the second term, the third term, and the fourth term. This arrangement ensures appropriate deformation analysis of the soil skeleton.

BRIEF DESCRIPTION OF THE DRAWINGS

FIG. 3 shows a soil foundation having four elements expressed by a 2×2 matrix as an analysis object in a concrete example;

FIG. 4 shows local nodes in each element;

FIG. 5 shows one concrete example of a file for inputting the settings of analysis conditions;

FIG. 6 shows one concrete example of a file for inputting the settings of analysis conditions;

FIG. 7 shows one concrete example of a file for inputting the settings of soils;

FIG. 8 shows one concrete example of a file for inputting the settings of a solid soil model;

FIG. 12 shows one concrete example of an output file;

BEST MODES OF CARRYING OUT THE INVENTION

One mode of carrying out the invention is described below in detail as a preferred embodiment with reference to the accompanied drawings.

Figure 1:
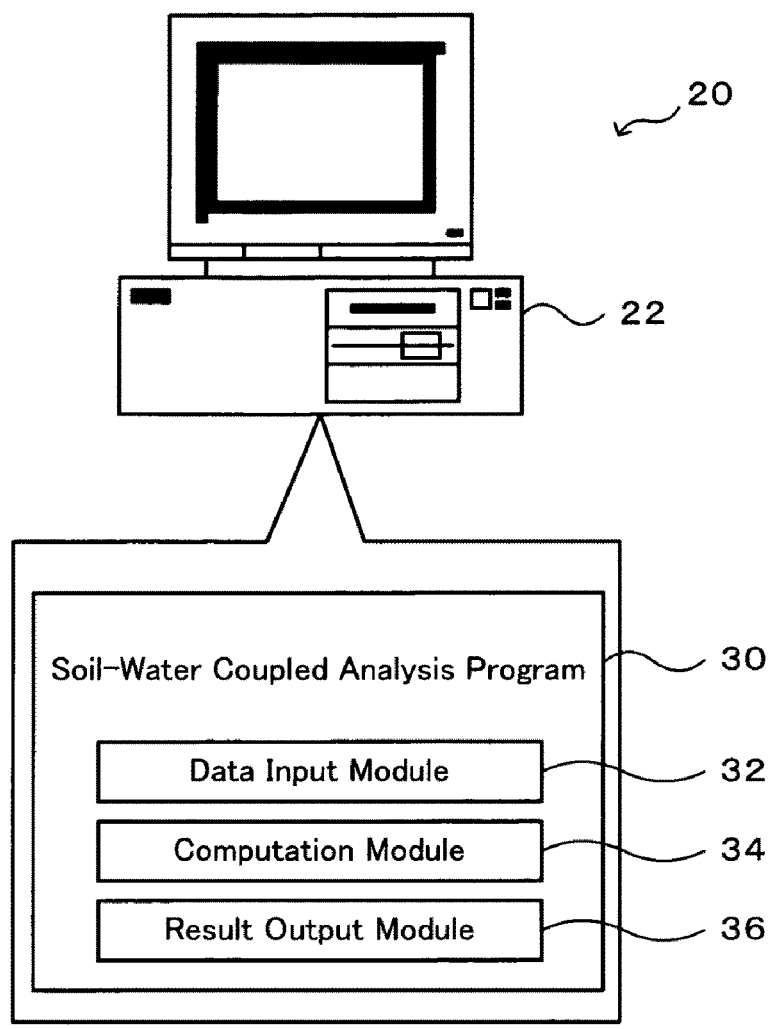
FIG. 1 schematically illustrates the configuration of a soil-water coupled analyzer 20 in one embodiment of the invention.

FIG. 1 schematically illustrates the configuration of a soil-water coupled analyzer 20 in one embodiment of the invention. The soil-water coupled analyzer 20 of the embodiment is constructed by installing a soil-water coupled analysis program 30 as application software in a general-purpose computer 22. The soil-water coupled analysis program 30 includes a data input module 32 that inputs data for setting the analysis conditions, the soil properties, and a solid soil model, a computation module 34 that analyzes the mechanical behaviors of saturated soil from the input data according to an elasto-plastic constitutive equation, and a result output module 36 that outputs the result of the analysis.

Figure 2:
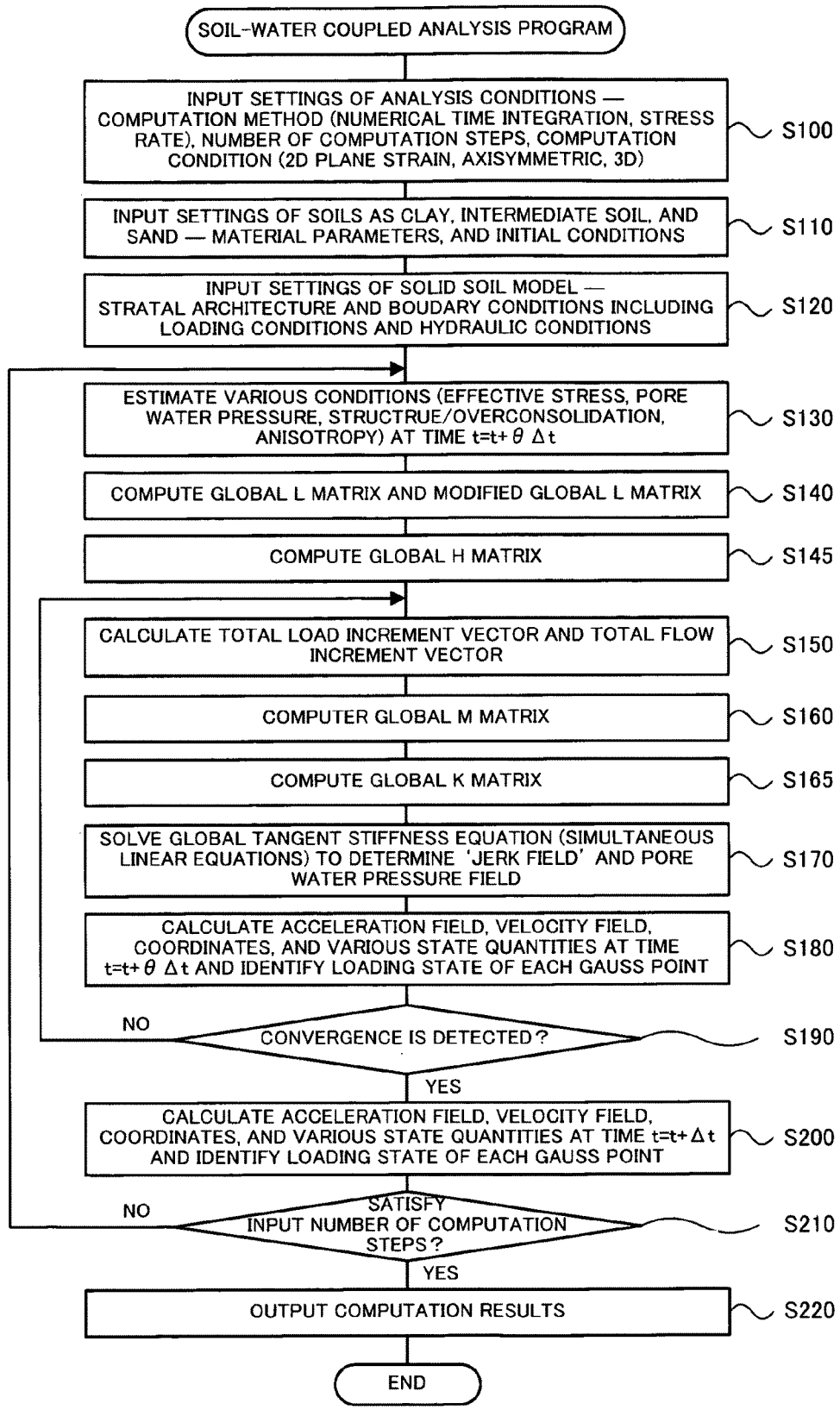
FIG. 2 is a flowchart showing a series of processing according to a soil-water coupled analysis program 30.

FIG. 2 is a flowchart showing a series of processing according to the soil-water coupled analysis program 30. The processing of the soil-water coupled analysis program 30 is described below in detail with reference to this flowchart. For the simplicity of explanation, a soil foundation as an analysis object in a concrete example is assumed to have four elements expressed by a 2×2 matrix. FIG. 3 shows the four elements in the concrete example. As shown in FIG. 3, element numbers 1, 2, 3, and 4 are allocated respectively to a lower left element, a lower right element, an upper left element, and an upper right element. Node numbers 1, 2, 3, 4, 5, 6, 7, 8, and 9 are allocated respectively to a lower left node, a lower center node, a lower right node, a middle left node, a middle center node, a middle right node, an upper left node, an upper center node, and an upper right node. Local node numbers 1, 2, 3, and 4 are allocated to respective local nodes in each element counterclockwise from a lower left local node as shown in FIG. 4. Internode numbers 1, 2, 3, and 4 are allocated to respective internodes in each element counterclockwise from a bottom internode as shown in FIG. 4.

The soil-water coupled analysis program 30 first inputs settings of analysis conditions (step S100). The settings of analysis conditions input here may include selection of a procedure for numerical time integration based on the difference method, an update frequency of time (the number of computation steps), and selection of a computation condition, such as two-dimensional plane strain, axisymmetric, or three-dimensional. FIGS. 5 and 6 show concrete examples of files for inputting the settings of analysis conditions. The inputs in the file of FIG. 5 include the setting of a computation condition selected among 'plane strain', 'axisymmetric', and 'three-dimensional', the setting of a deformation theory selected between 'small deformation theory' and 'finite deformation theory', the setting of an effective stress rate with objectivity in the finite deformation theory selected between 'Jaumann's rate of Cauchy stress' and 'Green-Naghdi's rate', the setting of convergence or non-convergence, the setting of a constitutive equation selected between 'original Cam-clay model with super-subloading yield surfaces and rotational hardening' and 'modified Cam-clay model with super-subloading yield surfaces and rotational hardening', the setting of state quantity output data selected between 'element average of Gauss points' and 'value of specified Gauss point', the setting of an output data format selected between 'Text' and 'Binary', and the setting of consideration or non-consideration of self weight. The inputs in the file of FIG. 6 include the settings of a current program number, the number of computation steps, a computation time DT per computation step (sec/step) (hereafter may be expressed as $\Delta t$), the number of divisions of excavated load in excavation, the number of divisions of distributed load in application of distributed load, an input file for soil material parameters and initial values, an input file for mesh data, specification of an output file for initial computation conditions used in execution of a next program, specification of an output file for coordinates, specification of an output file for state classification (unloading, loading (plastic compression/expansion, hardening/softening)), specification of an output file for a reactive force, specification of an output file for a pore water pressure, specification of an output file for a mean effective stress p' and a shear stress q, specification of an output file for a degree R of overconsolidation (=1/OCR: OCR represents an overconsolidation ratio), specification of an output file for a degree R* of structure, specification of an output file for a slope of a hardening/softening threshold line, specification of an output file for a plastic volume strain, specification of an output file for initial conditions, specification of an output file for a slope of a plastic compression/expansion threshold line, specification of an output file for an evolution degree of anisotropy, specification of an output file for an elapsed time, and output of file***.dat (preceding output file specifications).

The soil-water coupled analysis program 30 subsequently inputs the settings of soils as clay, intermediate soil, and sand with regard to the respective elements of the soil foundation (step S110). The settings of soils include material parameters and initial conditions. FIG. 7 shows one concrete example of a file for inputting the settings of soils. The inputs in the file of FIG. 7 include the number of elasto-plastic soil types, the number of elastic body types, specification of a plastic measure adopted in an evolution rule of structure, an intercept N of an isotropic normal consolidation line of remolded soil, a critical state constant M, a compression index $\lambda$, a swelling index $\kappa$, a Poisson's ratio $\nu$, a coefficient of permeability k, a specific gravity Gs of soil particles, an initial lateral pressure coefficient K0, an initial degree R0 of overconsolidation, an initial degree R*0 of structure, a normal consolidation index m, a U* shape, a structural degradation index a, a structural degradation index b, a structural degradation index c, a rotational hardening index br, a rotational hardening limit surface mb, an initial degree of anisotropy, an initial void ratio, a height of soil foundation/specimen, an initial overburden pressure of the soil foundation, an initial consolidation pressure of the specimen, a cell pressure (tensile: positive), and settings of a unit system (time, force, and length).

The soil-water coupled analysis program 30 then inputs the settings of a solid soil model (step S120). The settings of the solid soil model include conditions for elements of the soil model. FIG. 8 shows one concrete example of a file for inputting the settings of the solid soil model shown in FIGS. 3 and 4. In the file of FIG. 8, 1×6 data on the $1^{st}$ line successively show the number of elements, the number of nodes, and the number of elements with application of distributed load rate in the solid soil model, the number of nodes per element, the number of computation steps, and the number of elastic elements. In the file, 9×5 data on the $2^{nd}$ to the $10^{th}$ lines show each of node numbers and a type of boundary condition in an x-direction, a value of the boundary condition in the x-direction, a type of boundary condition in a y-direction, and a value of the boundary condition in the y-direction with regard to the corresponding node. The types of boundary condition include coordinate control (0), load rate control (1), displacement rate control (−1), and displacement acceleration control (−2). In the file of FIG. 8, 4×5 data on the 11$^{th}$ to the 14$^{th}$ lines show each of element numbers and global node numbers mapped to local node numbers with regard to the corresponding element (setting of a mapping of the local node number to the global node number). In the file, 9×3 data on the 15$^{th}$ to the 23$^{rd}$ lines show each of node numbers and a coordinate in the x-direction and a coordinate in the y-direction of the corresponding node. Data on the 24$^{th}$ line show the number of nodes requiring output of the reactive force, and data on the 25$^{th}$ line show their node numbers requiring output of the reactive force. There are two output directions of the reactive force, the x-direction and the y-direction with regard to each node. For example, output of the reactive force in the x-direction with regard to the node 7 is expressed as 7×2−1=13, and output of the reactive force in the y-direction with regard to the node 7 is expressed as 7×2=14. In the file, 2×6 data on the 26$^{th}$ and 27$^{th}$ lines show each of element numbers with application of distributed load rate and a side of application (internode of application), a value of the distributed load rate of its left node in the x-direction, a value of the distributed load rate in its left node in the y-direction, a value of the distributed load rate of its right node in the x-direction, and a value of the distributed load rate of its right node in the y-direction with regard to the corresponding element. In the file, 4×6 data on the 28$^{th}$ to the 31$^{st}$ lines show each of element numbers and an element number adjacent to the internode 1 of the corresponding element, an element number adjacent to the internode 2 of the corresponding element, an element number adjacent to the internode 3 of the corresponding element, an element number adjacent to the internode 4 of the corresponding element, and a soil type of the corresponding element (settings of a mapping of the internode number to the global element number and the soil type). Data on the 32$^{nd}$ line shows the number of conditions satisfying a fixed length between two nodes. When there is any condition satisfying the fixed length between two nodes, its condition number and specification of nodes involved in the condition are shown on a next line inserted immediately below the data on the 32$^{nd}$ line. Data on the 33$^{rd}$ line shows the number of conditions satisfying a fixed angle between three nodes. Data on the 34$^{th}$ line show a condition number satisfying the fixed angle between three nodes and specification of nodes involved in the condition. Data on the 35$^{th}$ line shows the number of conditions satisfying a fixed direction of a relative velocity of two nodes specified by relative position vectors of former two nodes and latter two nodes. Data on the 36$^{th}$ line show a condition number satisfying the fixed direction of the relative velocity of two nodes and specification of nodes involved in the condition. Data on the 37$^{th}$ line shows the number of conditions satisfying an equal displacement (velocity). When there is any condition satisfying the equal displacement (velocity), its condition number and specification relating to the condition are shown on a next line inserted immediately below the data on the 37$^{th}$ line. Data on the 38$^{th}$ line successively show the number of regular waves input into the model and the number of irregular waves input into the model. Data on the 39$^{th}$ line successively show a type of regular wave vibration, the number of nodes under influence of the regular wave vibration, and the amplitude and the period of the regular wave vibration. Data on the 40$^{th}$ line shows specification of nodes under influence of the regular wave vibration. There are two directions of the regular wave vibration, the x-direction and the y-direction with regard to each node. For example, the x-direction of the regular wave vibration with regard to the node 7 is expressed as 7×2−1=13, and the y-direction of the regular wave vibration with regard to the node 7 is expressed as 7×2=14. When there is any irregular wave input into the model, specification of the irregular wave is shown on a next line inserted immediately below the data on the 40$^{th}$ line.

After the data input, series of computations are performed with the input data (steps S130 to S210). The procedure of this embodiment adopts the Wilson's θ method for time integration, although another method, for example, the Newmark's β method, is also applicable. The procedure of this embodiment adopts the Tamura's model or the Christian's model of the finite element method of allocating the pore water pressure to the element center for spatial discretization, although another method, for example, the Sandhu's model of the finite element method of allocating the pore water pressure to the node or the mesh-free method, is also applicable. The following description regards computations according to the Wilson's θ method and the Tamura's model of the finite element method. A 'total position vector', a 'total velocity increment vector', and a 'total acceleration increment vector', and various conditions (for example, effective stress, pore water pressure, structure/overconsolidation, and anisotropy) at a time t=t+θΔt are estimated according to Equations (1) to (5) given below (step S130). These predictive calculations are performed for the purpose of convergence in a shorter time period and are not essential. In the case of omission of such predictive calculations, the values eventually determined at a time t=t or the initial values at an initial time are set to the values at the time t=t+θΔt. Each set of vector quantities of all nodes as in the left side or in each term of the right side of Equation (1) is expressed by a column vector having components as shown in Equation (6). Each set of scalar quantities of all elements as in the left side or in each term of the right side of Equation (4) is expressed by a column vector having components as shown in Equation (7).

$$\{x^N\}|_{t+\theta\Delta t} = \{x^N\}|_t + \{v^N(\theta\Delta t)\}|_t + \frac{1}{2}\{\dot{v}^N(\theta\Delta t)^2\}\Big|_t + \frac{1}{6}\{\ddot{v}^N(\theta\Delta t)^3\}\Big|_t \quad (1)$$

$$\{v^N(\theta\Delta t)\}|_{t+\theta\Delta t} = \{v^N(\theta\Delta t)\}|_t + \{\dot{v}^N(\theta\Delta t)^2\}\Big|_t + \frac{1}{2}\{\ddot{v}^N(\theta\Delta t)^3\}\Big|_t \quad (2)$$

$$\{\dot{v}^N(\theta\Delta t)^2\}\Big|_{t+\theta\Delta t} = \{\dot{v}^N(\theta\Delta t)^2\}\Big|_t + \{\ddot{v}^N(\theta\Delta t)^3\}\Big|_t \quad (3)$$

$$\{u\}|_{t+\theta\Delta t} = \{u\}|_t + \{\dot{u}(\theta\Delta t)\}|_t \quad (4)$$

$$A|_{t+\theta\Delta t} = A|_t + \dot{A}|_t (\theta\Delta t) \quad (5)$$

$\{x^N\}|_t$, $\{x^N\}|_{t+\theta\Delta t}$: column vector (total position vector) expressing set of position vectors of all nodes at time t=t or at time t=t+θΔt $\{v^N(\theta\Delta t)\}|_t$, $\{v^N(\theta\Delta t)\}|_{t+\theta\Delta t}$: column vector (total increment vector concerning velocity) given as production of θΔt and column vector (total velocity vector) $\{v^N\}$ expressing set of velocity vectors of all nodes at time t=t or at time t=t+θΔt $\{\dot{v}^N(\theta\Delta t)^2\}|_t$, $\{\dot{v}^N(\theta\Delta t)^2\}|_{t+\theta\Delta t}$: column vector (total increment vector concerning acceleration) given as the production of $(\theta\Delta t)^2$ and column vector (total acceleration vector) $\{\dot{v}^N\}$ expressing set of acceleration vectors of all nodes at time t=t or at time t=t+θΔt $\{\ddot{v}^N(\theta\Delta t)^3\}|_t$: column vector (total increment vector concerning jerk) given as production of $(\theta\Delta t)^3$ and column vector (total jerk vector) $\{\ddot{v}^N\}$ expressing set of jerk vectors of all nodes at time t=t $\{\dot{u}(\theta\Delta t)\}|_t$: column vector (total increment vector concerning pore water pressure) given as production of $\theta\Delta t$ and column vector (total pore water pressure rate vector) $\{\dot{u}\}$ expressing set of pore water pressure rate vectors of all elements at time t=t $\{u\}|_t$, $\{u\}|_{t+\theta\Delta t}$: column vector (total pore water pressure vector) $\{u\}$ expressing set of pore water pore vectors of all elements at time t=t or at time t=t+$\theta\Delta t$ A: state quantity, for example, effective stress tensor T', rotational hardening variable tensor β (tensor quantity), surface force vector t (vector quantity), pore water pressure u, degree R* of structure, degree R of overconsolidation (scalar quantity)

$A|_t$, $A|_{t+\theta\Delta t}$: state quantity A at time t=t or at time t=t+$\theta\Delta t$ $\dot{A}|_t$: rate of state quantity A at time t=t $$\{a^N\} = \begin{Bmatrix} a_1^1 \\ a_2^1 \\ a_r^1 \\ \vdots \\ a_1^j \\ a_2^j \\ a_r^j \\ \vdots \\ a_1^{NP} \\ a_2^{NP} \\ a_r^{NP} \end{Bmatrix} \quad (6)$$

$a_r^j$: r-direction component of $a^N$ at j-th node j: node number (j=1, 2, . . . , NP, NP: total number of nodes r: number of elements per node (r=2 for 2D plane strain condition and axisymmetric condition, r=3 for 3D condition)

$$\{\alpha\} = \begin{Bmatrix} \alpha^1 \\ \alpha^2 \\ \vdots \\ \alpha^i \\ \vdots \\ \alpha^{(NE-1)} \\ \alpha^{NE} \end{Bmatrix} \quad (7)$$

$\alpha^i$: value of α at i-th element i: element number (i=1, 2, . . . , NE, NE: total number of elements)

A global L matrix (global volume change rate matrix) and a modified global L matrix (modified global volume change rate matrix) are computed respectively according to Equation (8) and Equation (10) given below as matrices for converting the displacement rate of each node to the volume change rate of the soil skeleton over time (step S140). Each element of the global L matrix is shown by Equation (9). The global L matrix has NE rows and (NP×r) columns. According to the mapping of the global node number to the local node number specified in the setting of the solid soil model, the numeral '0' is set to a column component having an m-th node number mismatching with the global node number in an element L matrix for an element i shown in Equation (9). A Bv matrix as the constituent of the element L matrix is expressed by Equation (12) for the two-dimensional plane strain condition, by Equation (13) for the axisymmetric condition, and by Equation (14) for the three-dimensional condition. The modified global L matrix is created in the same manner as the global L matrix and has NE rows and (NP×r) columns.

$$L = \begin{bmatrix} L^{e1} \\ L^{e2} \\ \vdots \\ L^{ei} \\ \vdots \\ L^{e(NE-1)} \\ L^{eNE} \end{bmatrix} : \text{global } L \text{ matrix (global volume change rate matrix)} \quad (8)$$

$L^{ei} = [L^{i1}_{\ 1} L^{i1}_{\ 2} L^{i1}_{\ r} \ldots L^{im}_{\ 1} L^{im}_{\ 2} L^{im}_{\ 3} \ldots L^{ip}_{\ 1} L^{ip}_{\ 2} L^{ip}_{\ r}] = \int_{ve^i} [B_v] dv$: element L matrix for element i (element volume change rate matrix) (9)

m: local node number in element (m=1, 2, . . . , p)

p: number of nodes per element (p=4 for 2D plane strain condition and axisymmetric condition, p=8 for 3D condition)

$ve^i$: volume area occupied by element i $$L_{\theta n} = \begin{bmatrix} \gamma_{\theta n}^1 L^{e1} \\ \gamma_{\theta n}^2 L^{e2} \\ \vdots \\ \gamma_{\theta n}^i L^{ei} \\ \vdots \\ \gamma_{\theta n}^{(NE-1)} L^{e(NE-1)} \\ \gamma_{\theta n}^{NE} L^{eNE} \end{bmatrix} \quad (10)$$

(n = 1, 2, 3): modified global L matrix (modified global volume change rate matrix)

$$\gamma_{\theta 1}^i = -\frac{1}{2\theta\Delta t}\frac{k_i}{g} + \frac{1}{6}, \quad (11)$$

$$\gamma_{\theta 2}^i = 1 - \frac{1}{\theta\Delta t}\frac{k_i}{g},$$

$$\gamma_{\theta 3}^i = \frac{1}{6}\left(2 - \frac{3}{\theta\Delta t}\frac{k_i}{g}\right)$$

θ: parameter in Wilson's θ method $k_i$: coefficient of permeability of element i g: gravitational acceleration $[B_v] = [N^1_{,1} N^1_{,2} \ldots N^m_{,1} N^m_{,2} \ldots N^p_{,1} N^p_{,2}] (p=4)$ (12)

$N^m$: shape function regarding m-th node of element i $$[B_v] = \begin{bmatrix} N^1_{,1} + \dfrac{N^1}{x_1^G} & N^1_{,2} & \ldots & N^m_{,1} + \\ \dfrac{N^m}{x_1^G} & N^m_{,2} & \ldots & N^p_{,1} + \dfrac{N^p}{x_1^G} & N^p_{,2} \end{bmatrix} (p = 4) \quad (13)$$

$x_1^G$: distance in radial direction from rotational axis to Gauss point $[B_v] = [N^1_{,1} N^2_{,2} N^1_{,3} \ldots N^m_{,1} N^m_{,2} N^m_{,3} \ldots N^p_{,1} N^p_{,2} N^p_{,3}] (p=8)$ (14)

Figure 9:
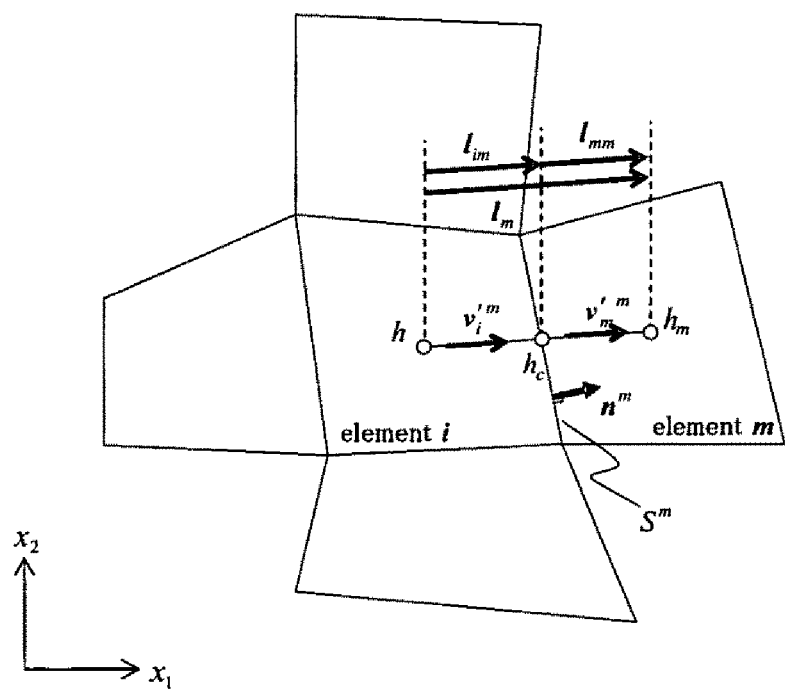
FIG. 9 shows a modeled flow of pore water under a two-dimensional plane strain condition.
Figure 10:
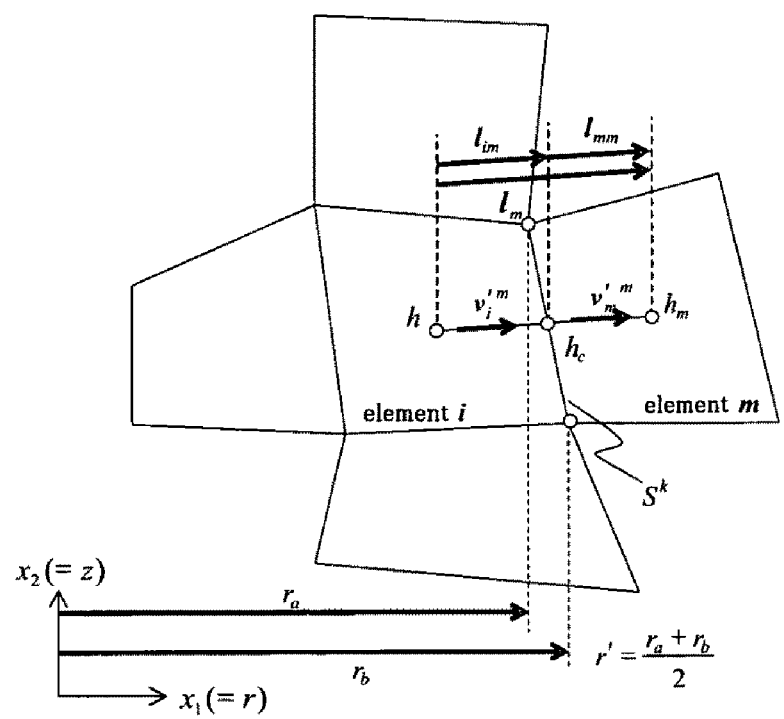
FIG. 10 shows a modeled flow of pore water under an axisymmetric condition.
Figure 11:
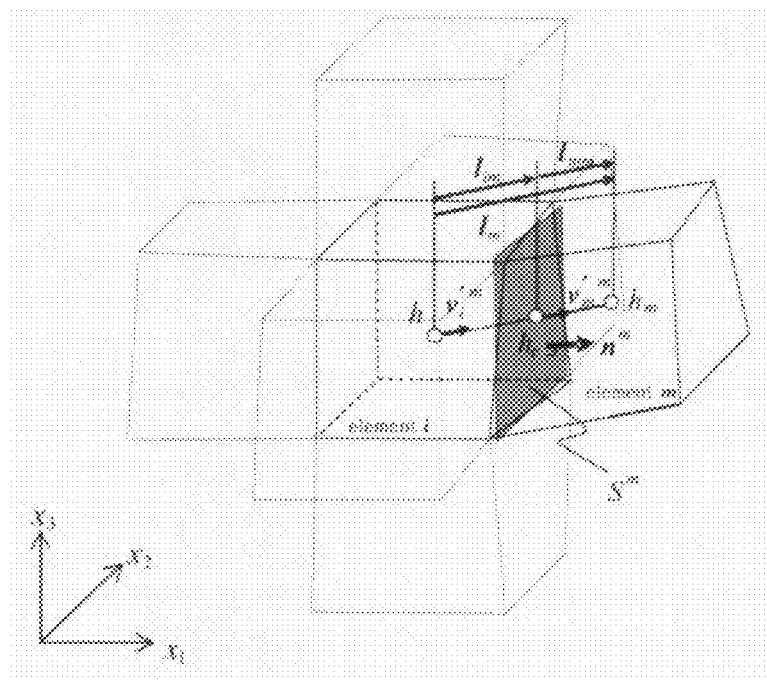
FIG. 11 shows a modeled flow of pore water under a three-dimensional condition.

The integrals like Equation (9) are performed according to the Gauss numeral integration method after conversion of a target analysis area in a global coordinate system into a local coordinate system as shown in Equation (15). Equation (15) shows volume integration for the three-dimensional condition. The integration is performed with consideration of a unit thickness in a perpendicular direction to the target analysis area for the two-dimensional plane strain condition, while being performed with consideration of the rotational symmetry about the axis for the axisymmetric condition.

$$\int\int\int f(x, y, z)dxdydz = \sum_{i=1}^{NG}\sum_{j=1}^{NG}\sum_{k=1}^{NG} w_i w_j w_k f \begin{pmatrix} x(\xi_i, \eta_j, \zeta_k), \\ y(\xi_i, \eta_j, \zeta_k), \\ z(\xi_i, \eta_j, \zeta_k) \end{pmatrix} J'(\xi_i, \eta_j, \zeta_k) \quad (15)$$

f=f (x, y, z): integrand in integral area in o-xyz coordinate system (for 3D condition)
J': Jacobian determinant for conversion from o-xyz into ξηζ local coordinate system having domain of [−1,1]
NG: number of Gauss points
$\xi_i$(i=1, ..., NG), $\eta_j$(j=1, ..., NG), $\zeta_k$(k=1, ..., NG): coordinates of Gauss points on ξ, η, ζ axes
$w_i$(i=1,...,NG), $w_j$(j=1,...,NG), $w_k$(k=1,...,NG): weights of respective Gauss points A global H matrix (global water permeability matrix) representing water permeability of the soil is then computed according to Equation (16) given below (step S145). The hydraulic boundary conditions, such as drained or undrained condition, are given by varying the components of an element H matrix shown in Equation (17). For example, the numeral '0' is set to a component in the element H matrix corresponding to an internode in the undrained condition. The global H matrix has NE rows and NE columns (r: the number of components per node). According to the mapping of the internode number of the element to the global element number specified in the setting of the solid soil model, the numeral '0' is set to a component having an m-th internode number mismatching with the global element number in the element H matrix for the element i shown in Equation (17). The last component in the element H matrix of the element i in Equation (17) is substituted into an i-th column component of the element i (i-th row) in the global H matrix. Each component on the right side of Equation (17) is expressed by Equation (18). The meanings of the respective symbols are defined in FIG. 9 for the two-dimensional plane strain condition, in FIG. 10 for the axisymmetric condition, and in FIG. 11 for the three-dimensional condition.

$$H = \begin{bmatrix} H^{e1} \\ H^{e2} \\ \vdots \\ H^{ei} \\ \vdots \\ H^{e(NE-1)} \\ H^{eNE} \end{bmatrix} : \text{global} \quad (16)$$

H matrix (global water permeability matrix)

$$H^{ei} = \left[\alpha_1^{ei} \ldots \alpha_m^{ei} \ldots \alpha_s^{ei} \; -\sum_{m=1}^{s}\alpha_m^{ei}\right]: \text{element} \quad (17)$$

H matrix (element water permeability matrix)

m internode number in element (m=1, 2, ..., s)
s: number of adjacent elements per element (s=4 for 2D plane strain condition and axisymmetric condition, s=6 for 3D condition)

$$\alpha_m^{ei} = \frac{\frac{k_i l_{im} \cdot n^m}{l_{im} \cdot l_{im}} \cdot \frac{k_m l_{mm} \cdot n^m}{l_{mm} \cdot l_{mm}}}{\frac{k_i l_{im} \cdot n^m}{l_{im} \cdot l_{im}} + \frac{k_m l_{mm} \cdot n^m}{l_{mm} \cdot l_{mm}}} S^m \quad \text{(no summation n)} \quad (18)$$

$k_i$: coefficient of permeability of element i
$k_m$: coefficient of permeability of element m
$n^m$: <2D plane strain condition and axisymmetric condition>
  outward (seen from element i) unit normal vector perpendicular to boundary side between element i and element m
  <3D condition>
  outward (seen from element i) unit normal vector perpendicular to two diagonal lines on boundary surface between element i and element m
$S^m$: <2D plane strain condition>
  distance between two nodes on boundary surface between element I and element m
  <axisymmetric condition>
  (distance between two nodes)×(distance r' from axis of rotational symmetry to center of gravity of side) on boundary surface between element i and element m
  <3D condision>
  projected area of boundary surface between element i and element m to plane that passes through center of gravity of four nodes defining boundary surface and has normal vector $n^m$
$l_{im}$: relative position vector from center of gravity of element i to center of gravity of element m on boundary surface
$l_{mm}$: relative position vector from center of gravity of element m to on boundary surface to center of gravity of element m A total load increment vector and a total flow increment vector at the time t=t+θΔt are calculated respectively according to Equation (19) and Equation (34) given below (step S150). A first term on the right side of Equation (19) is related to a nominal stress rate vector and is expressed by Equation (20). A second term on the right side of Equation (19) is related to the Green-Naghdi's rate and is expressed by Equation (21). An N matrix on the right side of Equation (20) and a B matrix on the right side of Equation (21) are expressed by Equations (22) and (23) for the two-dimensional plane strain condition, by Equations (24) and (25) for the axisymmetric condition, and by Equations (26) and (27) for the three-dimensional condition. The term of the nominal stress rate vector in Equation (20) is written as Equation (28) and is given as the sum of a traction force rate vector externally given through a boundary as a first term on the right side and an increment of a surface force vector accompanied with a geometry variation of the boundary as a second term on the right side. The traction force rate vector of the first term on the right side at the time t=t+θΔt is given by conversion of a traction force rate vector set as a boundary condition at the time t=t+θΔt according to Equation (29) in conformity with the Wilson's θ method. An n matrix included in the second term on the right side and related to an outward unit normal vector on a mechanical boundary of stress or stress rate is given by Equation (30) for the two-dimensional plane strain condition and the axisymmetric condition and by Equation (31) for the three-dimensional condition. A column vector including an effective stress component in a first term on the right side of Equation (21) is given by Equation (32) for the two-dimensional plane strain condition and the axisymmetric condition and by Equation (33) for the three-dimensional condition.

$$\{\dot{f}\theta\Delta t\}|_{t+\theta\Delta t} = \sum_{j=1}^{NS}{}'\{\dot{f}^j\theta\Delta t\}\Big|_{t+\theta\Delta t} + \sum_{i=1}^{NE}{}''\{\dot{f}^{ei}\theta\Delta t\}\Big|_{t+\theta\Delta t} : \text{total load} \quad (19)$$

increment vector at time $t$ $= t + \theta\Delta t$ $\sum_{j=1}^{NS}{}'$:

operation of adding value of node on j-th side (mechanical boundary of stress or stress rate) to value of corresponding global node, based on the mapping of local node number to global node number NS: number of planes on mechanical boundary (for 3D condition) or number of sides on mechanical boundary (for 2D plane strain condition and axisymmetric condition)

$\sum_{i=1}^{NE}{}''$:

operation of adding value of each node in i-th element to value of corresponding global node, based on the mapping of local node number to global node number $$\{\dot{f}\theta\Delta t\}|_{t+\theta\Delta t} = \int_a [N]^T \{\dot{s}_t\}|_{t+\theta\Delta t} da \times \theta\Delta t \quad (20)$$

$$\{\dot{f}^{ei}\theta\Delta t\}|_{t+\theta\Delta t} = \int_v [B]^T \{T'_\Omega\}|_{t+\theta\Delta t} dv \times \theta\Delta t \quad (21)$$

$$[N] = \begin{bmatrix} N^1 & 0 & \ldots & N^m & 0 & \ldots & N^p & 0 \\ 0 & N^1 & \ldots & 0 & N^m & \ldots & 0 & N^p \end{bmatrix} (p=4) \quad (22)$$

$$[B] = \begin{bmatrix} N^1_{,1} & 0 & \ldots & N^m_{,1} & 0 & \ldots & N^p_{,1} & 0 \\ 0 & N^1_{,2} & \ldots & 0 & N^m_{,2} & \ldots & 0 & N^p_{,2} \\ N^1_{,2} & N^1_{,1} & \ldots & N^m_{,2} & N^m_{,1} & \ldots & N^p_{,2} & N^p_{,1} \end{bmatrix} \quad (23)$$

$$[N] = \begin{bmatrix} N^1 & 0 & \ldots & N^m & 0 & \ldots & N^p & 0 \\ 0 & N^1 & \ldots & 0 & N^m & \ldots & 0 & N^p \end{bmatrix} (p=4) \quad (24)$$

-continued $$[B] = \begin{bmatrix} N^1_{,1} & 0 & \ldots & N^m_{,1} & 0 & \ldots & N^p_{,1} & 0 \\ 0 & N^1_{,2} & \ldots & 0 & N^m_{,2} & \ldots & 0 & N^p_{,2} \\ N^1_{,2} & N^1_{,1} & \ldots & N^m_{,2} & N^m_{,1} & \ldots & N^p_{,2} & N^p_{,1} \\ \frac{N^1}{x_1^G} & 0 & \ldots & \frac{N^m}{x_1^G} & 0 & \ldots & \frac{N^p}{x_1^G} & 0 \end{bmatrix} \quad (25)$$

$$[N] = \begin{bmatrix} N^1 & 0 & 0 & \ldots & N^m & 0 & 0 & \ldots & N^p & 0 & 0 \\ 0 & N^1 & 0 & \ldots & 0 & N^m & 0 & \ldots & 0 & N^p & 0 \\ 0 & 0 & N^1 & \ldots & 0 & 0 & N^m & \ldots & 0 & 0 & N^p \end{bmatrix} (p=8) \quad (26)$$

$$[B] = \begin{bmatrix} N^1_{,1} & 0 & 0 & \ldots & N^m_{,1} & 0 & 0 & \ldots & N^p_{,1} & 0 & 0 \\ 0 & N^1_{,2} & 0 & \ldots & 0 & N^m_{,2} & 0 & \ldots & 0 & N^p_{,2} & 0 \\ 0 & 0 & N^1_{,3} & \ldots & 0 & 0 & N^m_{,3} & \ldots & 0 & 0 & N^p_{,3} \\ N^1_{,2} & N^1_{,1} & 0 & \ldots & N^m_{,2} & N^m_{,1} & 0 & \ldots & N^p_{,2} & N^p_{,1} & 0 \\ 0 & N^1_{,3} & N^1_{,2} & \ldots & 0 & N^m_{,3} & N^m_{,2} & \ldots & 0 & N^p_{,3} & N^p_{,2} \\ N^1_{,3} & 0 & N^1_{,1} & \ldots & N^m_{,3} & 0 & N^m_{,1} & \ldots & N^p_{,3} & 0 & N^p_{,1} \end{bmatrix} \quad (27)$$

$$\{\dot{s}_t\}|_{t+\theta\Delta t} \times \theta\Delta t = \{\dot{t}\}|_{t+\theta\Delta t} \times \theta\Delta t + ([B_v] - [n]_{t+\theta\Delta t}[B]) \{v^N \theta\Delta t\}|_{t+\theta\Delta t} \{t\}|_{t+\theta\Delta t} \quad (28)$$

$$\{\dot{t}\}|_{t+\theta\Delta t} = \{\dot{t}\}|_t + \theta(\{\dot{t}\}|_{t+\Delta t} - \{\dot{t}\}|_t) \quad (29)$$

$\{\dot{s}_t\}|_{t+\theta\Delta t}$: nominal stress rate vector of i-th side specified as mechanical boundary at time t=t+θΔt $\{t\}|_{t+\theta\Delta t}$, $\{\dot{t}\}|_{t+\theta\Delta t}$: traction force vector acting on i-th side specified as mechanical boundary at time t=t+θΔt and its rate $[n]_{t+\theta\Delta t}$: matrix of respective components (direction cosine, $n_r$: r direction component) of outward unit normal vector at i-th side as mechanical boundary $$[n]_{t+\theta\Delta t} = [n_1^2 \, n_2^2 \, n_1 n_2] \quad (30)$$

$$[n]_{t+\theta\Delta t} = [n_1^2 \, n_2^2 \, n_3^2 \, n_1 n_2 \, n_2 n_3 \, n_3 n_1] \quad (31)$$

$$\{T'_\Omega\}|_{t+\theta\Delta t} = \Omega_c \begin{Bmatrix} -2T'_{12} \\ 2T'_{12} \\ T'_{11} 2T'_{22} \end{Bmatrix} \quad (32)$$

$T'_{ij}$: i,j components (i=1, 2, 3, j=1, 2, 3) of effective stress tensor T' at time t=t+θΔt $\Omega_c$: 2,1 components of material spin tencor $\Omega = \dot{R}R^T$ (R: rotation tensor) at time t=t+θΔt axisymmetric condition: value of 4$^{th}$ component=0

$$\{T'_\Omega\}|_{t+\theta\Delta t} = \begin{Bmatrix} 2(\Omega_2 T'_{13} - \Omega_3 T'_{12}) \\ 2(\Omega_3 T'_{12} - \Omega_1 T'_{23}) \\ 2(\Omega_1 T'_{23} - \Omega_2 T'_{13}) \\ -\Omega_2 T'_{13} + \Omega_2 T'_{23} + \Omega_3 (T'_{11} - T'_{22}) \\ \Omega_1 (T'_{22} + T'_{34}) - \Omega_2 T'_{12} + \Omega_3 T'_{13} \\ \Omega_1 T'_{12} + \Omega_2 (T'_{33} T'_{11}) - \Omega_3 T'_{23} \end{Bmatrix} \quad (33)$$

$T'_{ij}$: i,j components (i=1, 2, 3, j=1, 2, 3) of effective stress tensor T' at time t=t+θΔt $\Omega_1, \Omega_2, \Omega_3$: 3,2 components, 1,3 components, and 2,1 components of material spin tensor $\Omega = \dot{R}R^T$ (R: rotation tensor) at time $t=t+\theta\Delta t$ The total flow increment vector at the time $t=t+\theta\Delta t$ is expressed by Equation (34) given below and is obtained as the product of a total flow rate vector expressed by Equation (35) and $\theta\Delta t$.

$$\{\dot{f}_u(\theta\Delta t)\}|_{t+\theta\Delta t} = \{\dot{f}_u\}|_{t+\theta\Delta t} \times \theta\Delta t: \text{total flow increment vector at time } t=t+\theta\Delta t \quad (34)$$

$$\{\dot{f}_u\}|_{t+\theta\Delta t} = \quad (35)$$

$$\left\{\begin{array}{c} -\sum_{m=1}^{s} \rho_w g \alpha_m^{e1}(z_{cm}^1 - z_c^1) + q_1 \\ -\sum_{m=1}^{s} \rho_w g \alpha_m^{e2}(z_{cm}^2 - z_c^2) + q_2 \\ \vdots \\ -\sum_{m=1}^{s} \rho_w g \alpha_m^{ei}(z_{cm}^i - z_c^i) + q_i \\ \vdots \\ -\sum_{m=1}^{s} \rho_w g \alpha_m^{e(NE-1)}(z_{cm}^{(NE-1)} - z_c^{(NE-1)}) + q_{(NE-1)} \\ -\sum_{m=1}^{s} \rho_w g \alpha_m^{eNE}(z_{cm}^{NE} - z_c^{NE}) + q_{NE} \end{array}\right\}_{t+\theta\Delta t}$$

total flow rate vector at time $t = t + \theta\Delta t$ $\rho_w$: density of water
$z_c^i$: vertical coordinate of center of gravity of element i
$z_{cm}^i$: vertical coordinate of center of gravity of element m adjacent to element i
$q_i$: flow of water per unit time externally supplied to element i A global M matrix (global mass matrix) is computed according to Equation (36) given below (step S160). An element M matrix on the right side of Equation (37) is expressed by Equation (37). The global M matrix has (NP×r) rows and (NP×r) columns.

$$M = \sum_{i=1}^{NE'} M^{ei}: \text{global } M \text{ matrix(global mass matrix)} \quad (36)$$

$$\sum_{i=1}^{NE'}:$$

operation of allocating local node number of N matrix [N] at each of elements from element number i=1 to element number i=NE to global node numbers and combining the components from 0, based on the mapping of local node number to global node number specified in setting of solid soil model $M^{ei} = \int_v \rho[N]^T[N]dv$: element $M$ matrix (element mass matrix) of element $i$ \quad (37)

$\rho$: soil density of element i at time $$t = t + \theta\Delta t \left(\rho = \frac{e}{1+e}\rho_w + \frac{1}{1+e}\rho_s, \rho_s: \text{density of soil particles}\right)$$

A global K matrix (a global tangent stiffness matrix of soil skeleton) is computed according to Equation (38) given below (step S165). The global K matrix has (NP×r) rows and (NP×r) columns. An element K matrix as the constituent of the global K matrix is expressed by Equation (39). In Equation (39), a first term on the right side represents a tangent stiffness ensuring mechanical behavior of identified soil material (for example, sand or clay). A second term on the right side represents a contribution of a time change of soil shape to the tangent stiffness. A third term on the right side represents a contribution to the tangent stiffness under drastic influence of the acceleration to the soil skeleton, for example, impact load. A fourth term on the right side represents a contribution to the tangent stiffness under application of a body force. Relative differences given to the 'structural degradation index', the 'normal consolidation index', and the 'rotational hardening limit constant' among the material parameters ensure processing continuity from sand, intermediate soil, to clay. A $D^{ep}$ matrix (elasto-plastic matrix) included in the first term of Equation (39) is given by Equation (40) in the elasto-plastic state (in the loading state). Equation (40) is defined by Equations (41) and (42) for the two-dimensional plane strain condition, by Equations (43) and (44) for the axisymmetric condition, and by Equations (45) and (46) for the three-dimensional condition. The Dep matrix is given by Equation (47) in the elastic state. The symbols used in Equations (41) through (46) are defined by Equations (48). The symbols used in Equations (48) are given by one or combination of Equations (49).

$$K = \sum_{i=1}^{NE'} K^{ei}: \text{global } K \text{ matrix} \quad (38)$$

(global tangent stiffness matrix) of soil skeleton $$K^{ei} = \quad (39)$$

$$\int_v [B]^T[D^{ep}][B]dv + \int_v [N']^T[T_1][N']dv + \int_v \rho_w[N]^T[N]\{\dot{v}^{Ni}\}\Big|_{t+\theta\Delta t}$$

$$[B]_v dv - \int_v \rho_w[N]^T\{b\}[B_v]dv:$$

element K matrix (element tangent stiffness matix) of element i $\{\dot{v}^{Ni}\}|_{t+\theta\Delta t}$: column vector expressing acceleration vectors of respecfive nodes in element i at time $t=t+\theta\Delta t$ $\{b\}$: body force vector per unit mass $$[D^{ep}] = [D_1^{ep}] - [D_2^{ep}]: \text{elasto-plastic matrix} \quad (40)$$

$$[D_1^{ep}] = \begin{bmatrix} a'+b' & a' & 0 \\ a' & a'+b' & 0 \\ 0 & 0 & b'/2 \end{bmatrix} \quad (41)$$

$$[D_2^{ep}] = \frac{1}{e'}\begin{bmatrix} (c'\hat{\eta}_{11} - d')^2 & (c'\hat{\eta}_{11} - d)(c'\hat{\eta}_{22} - d') & c'\hat{\eta}_{12}(c'\hat{\eta}_{11} - d') \\ & (c'\hat{\eta}_{22} - d')^2 & c'\hat{\eta}_{12}(c'\hat{\eta}_{22} - d') \\ sym. & & (c'\hat{\eta}_{12})^2 \end{bmatrix} \quad (42)$$

$\hat{\eta}_{ij}$: i,j components of tensor $\hat{\eta}=\eta-\beta$ (i=1, 2, j=1, 2)

$$[D_1^{ep}] = \begin{bmatrix} a' + b' & a' & 0 & a' \\ a' & a' + b' & 0 & a' \\ 0 & 0 & b'/2 & 0 \\ a' & a' & 0 & a' + b' \end{bmatrix} \quad (43)$$

$$[D_2^{ep}] = \quad (44)$$
$$\frac{1}{e'}\begin{bmatrix} (c'\hat{\eta}_{11} - d')^2 & (c'\hat{\eta}_{11} - d')(c'\hat{\eta}_{22} - d') & c'\hat{\eta}_{12}(c'\hat{\eta}_{11} - d') & (c'\hat{\eta}_{11} - d')(c'\hat{\eta}_{33} - d') \\ & (c'\hat{\eta}_{22} - d')^2 & c'\hat{\eta}_{12}(c'\hat{\eta}_{22} - d') & (c'\hat{\eta}_{22} - d')(c'\hat{\eta}_{33} - d') \\ & & (c'\hat{\eta}_{12})^2 & c'\hat{\eta}_{12}(c'\hat{\eta}_{33} - d') \\ sym. & & & (c'\hat{\eta}_{33} - d')^2 \end{bmatrix}$$

$\hat{\eta}_{ij}$: i,j components of tensor $\hat{\eta}=\eta-\beta$ (i=1, 2, 3, j=1, 2, 3)

$$[D_1^{ep}] = \begin{bmatrix} a' + b' & a' & a' & & & \\ a' & a' + b' & a' & & 0 & \\ a' & a' & a' + b' & & & \\ & & & b'/2 & & \\ & 0 & & & b'/2 & \\ & & & & & b'/2 \end{bmatrix} \quad (45)$$

$$[D_2^{ep}] = \quad (46)$$
$$\frac{1}{e'}\begin{bmatrix} (c'\hat{\eta}_{11} - d')^2 & (c'\hat{\eta}_{11} - d')(c'\hat{\eta}_{22} - d') & (c'\hat{\eta}_{11} - d')(c'\hat{\eta}_{33} - d') & c'\hat{\eta}_{12}(c'\hat{\eta}_{11} - d') & c'\hat{\eta}_{23}(c'\hat{\eta}_{11} - d') & c'\hat{\eta}_{31}(c'\hat{\eta}_{11} - d') \\ & (c'\hat{\eta}_{22} - d')^2 & (c'\hat{\eta}_{22} - d)(c'\hat{\eta}_{33} - d') & c'\hat{\eta}_{12}(c'\hat{\eta}_{22} - d') & c'\hat{\eta}_{23}(c'\hat{\eta}_{22} - d') & c'\hat{\eta}_{31}(c'\hat{\eta}_{22} - d') \\ & & (c'\hat{\eta}_{33} - d')^2 & c'\hat{\eta}_{12}(c'\hat{\eta}_{33} - d') & c'\hat{\eta}_{23}(c'\hat{\eta}_{33} - d') & c'\hat{\eta}_{31}(c'\hat{\eta}_{33} - d') \\ sym. & & & (c'\hat{\eta}_{12})^2 & (c'\hat{\eta}_{12})(c'\hat{\eta}_{23}) & (c'\hat{\eta}_{12})(c'\hat{\eta}_{31}) \\ & & & & (c'\hat{\eta}_{23})^2 & (c'\hat{\eta}_{23})(c'\hat{\eta}_{31}) \\ & & & & & (c'\hat{\eta}_{31})^2 \end{bmatrix}$$

$\hat{\eta}_{ij}$: i,j components of tensor $\hat{\eta} = \eta - \beta$ (i=1, 2, 3, j=1, 2, 3)

$$[D_2^{ep}] = [0] \qquad (47)$$

$$\left.\begin{aligned} &a' = \tilde{K} - \frac{2}{3}\tilde{G}, \\ &b' = 2\tilde{G}, \\ &c' = 6\tilde{G}, \\ &d' = 6\tilde{K}\alpha, \\ &e' = 12\eta^{*2}\tilde{G} + \tilde{K}\alpha^2 + h \\ &\eta(=q/p') = \sqrt{\frac{3}{2}}\|\eta\| \left(= \sqrt{\frac{3}{2}\eta\cdot\eta}\right) : \text{effective stress ratio} \\ &\beta: \text{rotational hardening variable tensor(tensor defining direction and magnitude of anisotropy.The greater norm}\|\beta\|\text{represents the higher degree of anisotropy} \end{aligned}\right\} \qquad (48)$$

$$\left.\begin{aligned} &\tilde{K} = \frac{1+e}{\kappa}p'\left(=\frac{J(1+e_0)}{\kappa}p'\right) \\ &\tilde{G} = \frac{3(1-2\nu)}{2(1+\nu)}\tilde{K} \\ &\alpha = M_a^2 - \eta^2 \\ &h = Jp'\frac{M^2 + \eta^{*2}}{MD}(M_s^2 - \eta^2) \\ &D = \frac{(\lambda - \kappa)}{M(1+e_0)}: \text{dilatancy factor} \\ &p' = -\frac{1}{3}trT': \text{mean effective stress} \\ &\eta = T'/p' + I \\ &\eta^* = \sqrt{\frac{3}{2}}\|\hat{\eta}\| \end{aligned}\right\} \qquad (49)$$

$$M_a^2 = M^2 + \frac{3}{2}\beta\cdot\beta: \text{slope of threshold line between plastic compression and plastic expansion in } q - p' \text{ stress space} \qquad (50)$$

$$M_s^2 = M_a^2 + b_r\frac{4M\eta^{*2}}{M^2+\eta^{*2}}\left(m_b\eta^* - \sqrt{\frac{3}{2}}(\eta-\beta)\cdot\beta\right) - \\ MD\left(\frac{U^*}{R^*} - \frac{U}{R}\right)\sqrt{6\eta^{*2} + \frac{1}{3}\alpha^2} : \qquad (51)$$

slope of threshold line between hardening and softening in $p' - q$ stress space e: void ratio at time t=t+θΔt
$e_0$: void ratio at initial time t=0
J: determinant of deformation slope tensor of soil skeleton (giving infinitesimal volume ratio of soil skeleton at time t=t relative to initial time t=0), J=1 for small deformation analysis
λ: compression index
κ: swelling index
M: critical state constant
ν: Poisson's ratio
I: unit tensor
q=η×p': shear stress Equation (50) and Equation (51) respectively show the slope of a threshold line between plastic compression and plastic expansion and the slope of a threshold line between hardening and softening in the p'-q stress space. A plastic stretching norm as the plasticity measure is adopted for the expressions of Equations (50) and (51) as shown in Equations (52) and (53) in the evolution rule, which specifies a process of lowering the degree R* of structure (0<R*≦1: the value of R* closer to 0 represents the more highly structured) and a process of losing the degree R of overconsolidation (0<R≦1: the value of R closer to 0 represents the higher level of overconsolidation) in the structure of the soil skeleton. The plasticity measure may be a shear component of the plastic stretching or a plastic power given as the inner product of the effective stress tensor and the plastic stretching, according to the type of soil. In small deformation analysis, the plastic stretching is specified by a plastic strain rate. 'U*' in Equation (52) and 'U' in Equation (53) are nonnegative functions and are given, for example, by Equations (54) and (55). Equation (56) is adopted for the evolution rule of the rotational hardening variable tensor representing the anisotropy.

$$\dot{R}^* = JU^*\|D^p\| = JU^*\sqrt{6\eta^{*2} + \frac{1}{3}\alpha^2}\frac{6\tilde{G}\hat{\eta}\cdot D - \tilde{K}\alpha(trD)}{12\eta^{*2}\tilde{G} + \tilde{K}\alpha^2 + h} \qquad (52)$$

$$\dot{R} = JU\|D^p\| = JU\sqrt{6\eta^{*2} + \frac{1}{3}\alpha^2}\frac{6\tilde{G}\hat{\eta}\cdot D - \tilde{K}\alpha(trD)}{12\eta^{*2}\tilde{G} + \tilde{K}\alpha^2 + h} \qquad (53)$$

$\dot{R}^*$, $\dot{R}$: rates of R* and R (material time derivation)
$D^p$: plastic stretching
D: streching $$U^* = \frac{a}{D}R^{*b}(1-R^*)^c \qquad (54)$$

$$U = -\frac{m}{D}\ln R \qquad (55)$$

a, b, c: structural degradation indexes (material parameters for controlling the potential for degrading the structure
m: normal consolidation index (material parameters for controlling the potential for loss of overconsolidation or the potential for normal consolidation $$\overset{\circ}{\beta}(=\dot{\beta} + \beta\Omega - \Omega\beta) = J\frac{b_r}{D}\sqrt{\frac{2}{3}}\|D_s^p\|\|\hat{\eta}\|\left(m_b\frac{\hat{\eta}}{\|\hat{\eta}\|} - \beta\right) \qquad (56)$$

$$= J\frac{b_r}{D}2\eta^{*2}\frac{6\tilde{G}\hat{\eta}\cdot D - \tilde{K}\alpha(trD)}{12\eta^{*2}\tilde{G} + \tilde{K}\alpha^2 + h}\|\hat{\eta}\|\left(m_b\frac{\hat{\eta}}{\|\hat{\eta}\|} - \beta\right)$$

$\overset{\circ}{\beta}$: Green-Nagdhi's rate of β
$\dot{\beta}$: rate of β
$b_r$: rotational hardening index (material parameter for controlling the potential for evolution of anisotropy β
$m_b$: rotational hardening limit constant (material parameter for representing evolution limit of anisotropy An N' matrix and a $T_1$ matrix included in a second term on the right side of Equation (39) are given by Equations (57) and (58) for the two-dimensional plane strain condition, by Equations (59) and (60) for the axisymmetric condition, and by Equations (61) and (62) for the three-dimensional condition.

$$[N'] = \begin{bmatrix} N_{,1}^1 & 0 & \ldots & N_{,1}^m & 0 & \ldots & N_{,1}^p & 0 \\ 0 & N_{,2}^1 & \ldots & 0 & N_{,2}^m & \ldots & 0 & N_{,2}^p \\ N_{,2}^1 & 0 & \ldots & N_{,2}^m & 0 & \ldots & N_{,2}^p & 0 \\ 0 & N_{,1}^1 & \ldots & 0 & N_{,1}^m & \ldots & 0 & N_{,1}^p \end{bmatrix} \quad (57)$$

$$[T_1] = \begin{bmatrix} 0 & T_{11} & T_{12} & 0 \\ T_{22} & 0 & 0 & -T_{12} \\ T_{12} & 0 & 0 & -T_{11} \\ 0 & T_{12} & -T_{22} & 0 \end{bmatrix} \quad (58)$$

$T_{ij}$: i,j components (i=1, 2, j=1, 2) of total stress tensor $T(=T'-uI)$ at time $t=t+\theta\Delta t$ (u: pore water pressure, compression: positive)

$$[N'] = \begin{bmatrix} N_{,1}^1 & 0 & \ldots & N_{,1}^m & 0 & \ldots & N_{,1}^p & 0 \\ 0 & N_{,2}^1 & \ldots & 0 & N_{,2}^m & \ldots & 0 & N_{,2}^p \\ N_{,2}^1 & 0 & \ldots & N_{,2}^m & 0 & \ldots & N_{,2}^p & 0 \\ 0 & N_{,1}^1 & \ldots & 0 & N_{,1}^m & \ldots & 0 & N_{,1}^p \\ \dfrac{N^1}{x_1^G} & 0 & \ldots & \dfrac{N^m}{x_1^G} & 0 & \ldots & \dfrac{N^p}{x_1^G} & 0 \end{bmatrix} \quad (59)$$

$$[T_1] = \begin{bmatrix} 0 & T_{11} & -T_{12} & 0 & T_{11} \\ T_{22} & 0 & 0 & -T_{12} & T_{22} \\ T_{12} & 0 & 0 & -T_{11} & T_{12} \\ 0 & T_{12} & -T_{22} & 0 & T_{12} \\ T_{33} & T_{33} & 0 & 0 & 0 \end{bmatrix} \quad (60)$$

$T_{ij}$: i,j components (i=1, 2, 3, j=1, 2, 3) of total stress tensor T at time $t=t+\theta\Delta t$ $$[N'] = \begin{bmatrix} N_{,1}^1 & 0 & 0 & \ldots & N_{,1}^m & 0 & 0 & \ldots & N_{,1}^p & 0 & 0 \\ 0 & N_{,2}^1 & 0 & \ldots & 0 & N_{,2}^m & 0 & \ldots & 0 & N_{,2}^p & 0 \\ 0 & 0 & N_{,3}^1 & \ldots & 0 & 0 & N_{,3}^1 & \ldots & 0 & 0 & N_{,3}^p \\ N_{,2}^1 & 0 & 0 & \ldots & N_{,2}^m & 0 & 0 & \ldots & N_{,2}^p & 0 & 0 \\ 0 & N_{,1}^1 & 0 & \ldots & 0 & N_{,1}^m & 0 & \ldots & 0 & N_{,1}^p & 0 \\ 0 & N_{,3}^1 & 0 & \ldots & 0 & N_{,3}^m & 0 & \ldots & 0 & N_{,3}^p & 0 \\ 0 & 0 & N_{,2}^1 & \ldots & 0 & 0 & N_{,2}^m & \ldots & 0 & 0 & N_{,2}^p \\ 0 & 0 & N_{,1}^1 & \ldots & 0 & 0 & N_{,1}^m & \ldots & 0 & 0 & N_{,1}^p \\ N_{,3}^1 & 0 & 0 & \ldots & N_{,3}^m & 0 & 0 & \ldots & N_{,3}^p & 0 & 0 \end{bmatrix} \quad (61)$$

$$[T_1] = \begin{bmatrix} 0 & T_{11} & T_{11} & -T_{12} & 0 & 0 & 0 & 0 & -T_{13} \\ T_{22} & 0 & T_{22} & 0 & -T_{12} & -T_{23} & 0 & 0 & 0 \\ T_{33} & T_{33} & 0 & 0 & 0 & 0 & -T_{23} & -T_{13} & 0 \\ T_{12} & 0 & T_{12} & 0 & -T_{11} & -T_{13} & 0 & 0 & 0 \\ 0 & T_{12} & T_{12} & -T_{22} & 0 & 0 & 0 & 0 & -T_{23} \\ T_{23} & T_{23} & 0 & 0 & 0 & -T_{22} & -T_{12} & 0 \\ T_{23} & 0 & T_{23} & 0 & -T_{13} & -T_{33} & 0 & 0 & 0 \\ 0 & T_{31} & T_{31} & -T_{23} & 0 & 0 & 0 & 0 & -T_{33} \\ T_{31} & T_{31} & 0 & 0 & 0 & 0 & -T_{12} & -T_{11} & 0 \end{bmatrix} \quad (62)$$

$T_{ij}$: i,j components (i=1, 2, 3, j=1, 2, 3) of total stress tensor T at time $t=t+\theta\Delta t$ After calculation of the global M matrix and the global K matrix in the above manner, an unknown 'jerk field' and a pore water pressure field are determined according to a global tangent stiffness equation (simultaneous linear equations) given as Equation (63) below under a geometric boundary condition with regard to the displacement, the displacement rate, or the acceleration, a mechanical boundary condition with regard to the stress or the stress rate, and hydraulic boundary conditions with regard to the pore water pressure or the total water head and the flow of pore water (step S170). Equation (63) is given by computing a time derivative term according to an implicit method (finite difference method) in simultaneous second-order ordinary differential equations (Equation (64)), which are eventually obtained by finite element discretization of the weak form of the motion equations of rate type and modeling of the soil-water coupled equation with consideration of the influence of an inertial term. Equation (63) represents the simultaneous linear equations to be (eventually) solved with application of the Wilson's θ method to the deformation filed and the trapezoidal rule to the pore water pressure. The total load increment vector, the total flow increment vector, the global M matrix, and the global K matrix are updated through iterative computations in a time step between the time t=t and the time $t=t+\theta\Delta t$. Equation (64) applies the material time derivation of the soil skeleton to the motion equations and accordingly has a characteristic 'jerk' term or second-order derivative term on the time of a velocity vector as an explanatory variable. This characteristic gives a rate type constitutive equation of the soil skeleton and allows consideration of a geometric change of the soil foundation. This enables large deformation analysis requiring accurate measurement of a volume change rate of soil between deformation to failure or with regard to a behavior after the failure. For introduction of this jerk term, Equations (66) to (68) are introduced with respect to deformation based on the concept of a linear acceleration method as the basis of the Wilson's θ method. In the case of a response having little effect of the acceleration, Equation (64) is equal to simultaneous first-order ordinary differential equations obtained by static analysis. This means no requirement for the selective use of dynamic analysis or static analysis. Under a constraint condition of, for example, a fixed length between two nodes or a fixed angle between three nodes, imposed on the internode, the Lagrange's method of undetermined multipliers is adopted to solve Equation (64) with consideration of the constraint condition. The geometric boundary condition on the displacement, the displacement rate, or the acceleration set at the time $t=t+\theta\Delta t$ is converted into a jerk vector at the time $t=t+\theta\Delta t$ by Equation (69) in the case of being given as a difference of position vectors or a displacement vector, by Equation (70) in the case of being given as a velocity vector, and by Equation (71) in the case of being given as an acceleration vector.

$$\begin{bmatrix} \frac{1}{(\theta\Delta t)^2}M + \frac{1}{6}K & -2L^T \\ -L_{\theta 1} & H \times \theta\Delta t \end{bmatrix} \begin{Bmatrix} \{\dddot{v}^N(\theta\Delta t)^3\}|_{t+\theta\Delta t} \\ \{u\}|_{t+\theta\Delta t} \end{Bmatrix} = \tag{63}$$

$$\begin{Bmatrix} \{f(\theta\Delta t)\}|_{t+\theta\Delta t} - K[\{v^N(\theta\Delta t)\}|_t + \{\dot{v}^N(\theta\Delta t)^2\}|_t + \\ \frac{1}{3}\{\ddot{v}^N(\theta\Delta t)^3\}|_t] - 2L^T[\{u\}|_t + \frac{1}{2}\{\dot{u}(\theta\Delta t)\}|_t] \\ \{f_u(\theta\Delta t)\}|_{t+\theta\Delta t} + L\{v^N(\theta\Delta t)\}|_t + \\ L_{\theta 2}\{\dot{v}^N(\theta\Delta t)^2\}|_t + L_{\theta 3}\{\ddot{v}^N(\theta\Delta t)^3\}|_t \end{Bmatrix}$$

$\{\dddot{v}^N(\theta\Delta t)^3\}|_{t+\theta\Delta t}$ : total increment vector concerning jerk at time $t = t + \theta\Delta t$ $$\begin{bmatrix} M & 0 \\ 0 & 0 \end{bmatrix} \frac{d^2}{dt^2} \begin{Bmatrix} \{v^N\} \\ \{u\} \end{Bmatrix} + \begin{bmatrix} 0 & -L^T \\ L' & 0 \end{bmatrix} \frac{d}{dt} \begin{Bmatrix} \{v^N\} \\ \{u\} \end{Bmatrix} + \begin{bmatrix} K & 0 \\ -L & H \end{bmatrix} \begin{Bmatrix} \{v^N\} \\ \{u\} \end{Bmatrix} = \tag{64}$$

$$\begin{Bmatrix} \{\dot{f}\} \\ \{\dot{f}_u\} \end{Bmatrix}$$

$$L' = \frac{1}{g} \begin{bmatrix} k_1 L^{e1} \\ & k_2 L^{e2} \\ & & \vdots \\ & & & k_n L^{ei} \\ & & & & \vdots \\ & & & & & k_{(NE-1)} L^{e(NE-1)} \\ & & & & & & k_{NE} L^{eNE} \end{bmatrix} \tag{65}$$

secondary modified global $L$ matrix (secondary modified global volume change rate matrix)

$$\{v^N\}|_{t+\theta\Delta t} = \{v^N\}|_t + \frac{1}{2}\{\dot{v}^N\}\Big|_t \theta\Delta t + \frac{1}{2}\{\ddot{v}^N\}\Big|_{t+\theta\Delta t} \theta\Delta t \tag{66}$$

$$\{v^N\}|_{t+\theta\Delta t} = \{v^N\}|_t + \{\dot{v}^N\}|_t \theta\Delta t + \frac{1}{3}\{\ddot{v}^N\}\Big|_t (\theta\Delta t)^2 + \frac{1}{6}\{\dddot{v}^N\}\Big|_{t+\theta\Delta t}(\theta\Delta t)^2 \tag{67}$$

$$\{x^N\}|_{t+\theta\Delta t} = \{x^N\}|_t + \{v^N\}\Big|_t \theta\Delta t + \frac{1}{2}\{\dot{v}^N\}\Big|_t (\theta\Delta t)^2 + \frac{1}{8}\{\ddot{v}^N\}\Big|_t (\theta\Delta t)^3 + \frac{1}{24}\{\dddot{v}^N\}\Big|_{t+\theta\Delta t}(\theta\Delta t)^3 \tag{68}$$

$$\dddot{v}^{Njr}|_{t+\theta\Delta t}(\theta\Delta t)^3 = \dddot{v}^{Njr}|_t(\theta\Delta t)^3 + 24\theta^4(x^{Njr}|_{t+\Delta t} - x^{Njr}|_t) - 24\theta^3 v^{Njr}|_t(\theta\Delta t) - 12\theta^2 \dot{v}^{Njr}|_t(\theta\Delta t)^2 - 4\theta \ddot{v}^{Njr}|_t(\theta\Delta t)^3 \tag{69}$$

$$\dddot{v}^{Njr}|_{t+\theta\Delta t}(\theta\Delta t)^3 = \dddot{v}^{Njr}|_t(\theta\Delta t)^3 + 6\theta^3(v^{Njr}|_{t+\Delta t} - v^{Njr}|_t)(\theta\Delta t) - 6\theta^2 \dot{v}^{Njr}|_t(\theta\Delta t)^2 - 3\theta \ddot{v}^{Njr}|_t(\theta\Delta t)^3 \tag{70}$$

$$\dddot{v}^{Njr}|_{t+\theta\Delta t}(\theta\Delta t)^3 = \dddot{v}^{Njr}|_t(\theta\Delta t)^3 + 2\theta^2\{\dot{v}^{Njr}|_{t+\Delta t}(\theta\Delta t)^2 - \dot{v}^{Njr}|_t(\theta\Delta t)^2\} - 2\theta \ddot{v}^{Njr}|_t(\theta\Delta t)^3 \tag{71}$$

$x^{Njr}|_{t|\Delta t}$: r-direction component of position vector of j-th node at time $t=t+\Delta t$ set as boundary condition $v^{Njr}|_{t+\Delta t}$: r-direction component of velocity vector of j-th node at time $t=t+\Delta t$ set as boundary condition $\dot{v}^{Njr}|_{t+\Delta t}$: r-direction component of acceleration vector of j-th node at time $t=t+\Delta t$ set as boundary condition $x^{Njr}|_t$: r-direction component of position vector of j-th node at time $t=t$ $v^{Njr}|_t$: r-direction component of velocity vector of j-th node at time $t=t+\Delta t$ $\dot{v}^{Njr}|_t$: r-direction component of acceleration vector of j-th node at time $t=t+\Delta t$ $\ddot{v}^{Njr}|_t$: r-direction component of jerk vector of j-th node at time $t=t+\Delta t$ $\dddot{v}^{Njr}|_{t+\theta\Delta t}$: r-direction component of converted jerk vector of j-th node at time $t=t+\theta\Delta t$ The soil-water coupled analysis program 30 then calculates an acceleration field, a velocity field, coordinates, and various state quantities at the time $t=t+\theta\Delta t$ and identifies a loading state of each Gauss point (step S180). A total increment vector concerning acceleration, a total increment vector concerning velocity, and a coordinate vector at the time $t=t+\theta\Delta t$ are calculated from the total jerk increment vector at the time $t=t+\theta\Delta t$ in Equation (63) and the various geometric quantities at the time $t=t$ according to Equations (72) to (74), which are led from Equations (66) to (68). Respective state quantities A, for example, effective stress, degree R* of structure, degree R of overconsolidation, and anisotropy, at the time $t=t+\theta\Delta t$ are computed by Equation (75). For example, an effective stress rate at each Gauss point in a certain element at the time $t=t+\theta\Delta t$ is calculated according to Equation (76) from velocity vectors of nodes in the certain element out of the total increment vector concerning velocity given by Equation (73). Subsequent application of Equation (75) determines the effective stress. The rates of the degree of structure, the degree of overconsolidation, and the anisotropy are determined according to Equations (52), (53), and (56) for the Gauss points in the elasto-plastic state and are set equal to 0 for the Gauss points in the elastic state. In the modified Cam-clay model with super-subloading yield surfaces and rotational hardening, the 'plastic volume strain' at the time $t=t+\theta\Delta t$ is calculated by Equation (80) for the Gauss points in the elasto-plastic state and is kept to a previous value calculated in the last elasto-plastic state for the Gauss points in the elastic state. In the elastic state, the degree R of overconsolidation at the time $t=t+\theta\Delta t$ is computable according to an equation that is obtained by solving Equation (80) for the degree R of overconsolidation. The pore water pressure at the time $t=t+\theta\Delta t$ is directly determined by the global tangent stiffness equation given as Equation (63). The rate of the pore water pressure is determined by inversely applying Equation (75). The loading state of each Gauss point in the soil element is identified as the elasto-plastic state or the elastic state, based on the effective stress and the stretching of the Gauss point in the soil element. The loading state of a Gauss point is identified as the elasto-plastic state upon satisfaction of a loading criterion given by Equation (81) as the numerator of the plastic multiplier. A column vector of the stretching is obtained by Equation (82). The components of the column vector at the time $t=t+\theta\Delta t$ are expressed by Equation (83) for the two-dimensional plane strain condition, by Equation (84) for the axisymmetric condition, and by Equation (85) for the three-dimensional condition.

$$\{\dot{v}^N(\theta\Delta t)^2\}|_{t+\theta\Delta t} = \{\dot{v}^N(\theta\Delta t)^2\}|_t + \frac{1}{2}\{\ddot{v}^N(\theta\Delta t)^3\}|_t + \frac{1}{2}\{\dddot{v}^N(\theta\Delta t)^3\}\Big|_{t+\theta\Delta t} \tag{72}$$

$$\{v^N(\theta\Delta t)\}|_{t+\theta\Delta t} = \tag{73}$$
$$\{v^N(\theta\Delta t)\}|_t + \{\dot{v}^N(\theta\Delta t)^2\}|_t + \frac{1}{3}\{\ddot{v}^N(\theta\Delta t)^3\}\Big|_t + \frac{1}{6}\{\dddot{v}^N(\theta\Delta t)^3\}\Big|_{t+\theta\Delta t}$$

-continued $$\{x^N\}|_{t+\theta\Delta t} = \{x^N\}|_t + \{v^N(\theta\Delta t)^2\}|_t + \frac{1}{2}\{\dot{v}^N(\theta\Delta t)^2\}|_t + \frac{1}{8}\{\ddot{v}^N(\theta\Delta t)^3\}|_t + \frac{1}{24}\{\dddot{v}^N(\theta\Delta t)^3\}|_{t+\theta\Delta t} \quad (74)$$

$$A|_{t+\theta\Delta t} = A|_t + \frac{1}{2}(\dot{A}|_{t+\theta\Delta t} + \dot{A}|_t)(\theta\Delta t) \quad (75)$$

$A|_t, A|_{t+\theta\Delta t}$: state quantities A at time t=t and at time t=t+θΔt
$\dot{A}|_t, \dot{A}|_{t+\theta\Delta t}$: rates of state quantities A at time t=t and at time t=t+θΔt $$\{\dot{T}'^i\}|_{t+\theta\Delta t} \times \theta\Delta t = [D^{ep}][B]\{v^{Ni}\theta\Delta t\}|_{t+\theta\Delta t} - \{T'_\Omega\}|_{t+\theta\Delta t} \times \theta\Delta t \quad (76)$$

$\{v^{Ni}\theta\Delta t\}|_{t+\Delta t}$: column vector expression of velocity vectors at respective nodes in element i at time t=t+θΔt $\{\dot{T}'\}|_{t+\theta\Delta t}$: column vector expression of components of effective stress rate tensor $\dot{T}'$ at respective Gauss points in element i at time t=t+θΔt <2D plane strain condition> (77)

$$\{\dot{T}'\}|_{t+\theta\Delta t} = \begin{Bmatrix} \dot{T}'_{11} \\ \dot{T}'_{22} \\ \dot{T}'_{12} \end{Bmatrix}\Bigg|_{t+\theta\Delta t}$$

<axisymetrix condition> (78)

$$\{\dot{T}'\}|_{t+\theta\Delta t} = \begin{Bmatrix} \dot{T}'_{11} \\ \dot{T}'_{22} \\ \dot{T}'_{12} \\ \dot{T}'_{33} \end{Bmatrix}\Bigg|_{t+\theta\Delta t}$$

<3D condition> (79)

$$\{\dot{T}'\}|_{t+\theta\Delta t} = \begin{Bmatrix} \dot{T}'_{11} \\ \dot{T}'_{22} \\ \dot{T}'_{33} \\ \dot{T}'_{12} \\ \dot{T}'_{23} \\ \dot{T}'_{31} \end{Bmatrix}\Bigg|_{t+\theta\Delta t}$$

$$\varepsilon_v^p \left( = -\int_0^t JtrD^p\,d\tau \right) = \quad (80)$$

$$MD\ln\frac{p'}{p'_0} + MD\ln\frac{M^2+\eta^{*2}}{M^2} + MD\ln R^* - MD\ln R:$$

subloading yield surface in modified Clam-clay model $\varepsilon_v^p$: 'plastic volume strain' (compression: positive)
$p'_0$: p'(>0) value of making the normal yield surface (modified Can-clay yield surface) at the initial time t=0 satisfy η*=0 in the p'–q stress space $$\frac{6M\tilde{G}}{M^2+\eta^{*2}}(\eta-\beta)\cdot D - \tilde{K}\alpha(trD) > 0 \quad (81)$$

$\{D\} = [B]\{v^{Ni}\}$: (82)
column vector expression of components of stretching tensor D in element i <2D plane strain condition> (83)

$$\{D\}|_{t+\theta\Delta t} = \begin{Bmatrix} D_{11} \\ D_{22} \\ 2D_{12} \end{Bmatrix}\Bigg|_{t+\theta\Delta t}$$

<axisymmetric condition> (84)

$$\{D\}|_{t+\theta\Delta t} = \begin{Bmatrix} D_{11} \\ D_{22} \\ 2D_{12} \\ D_{33} \end{Bmatrix}\Bigg|_{t+\theta\Delta t}$$

<3D condition> (85)

$$\{D\}|_{t+\theta\Delta t} = \begin{Bmatrix} D_{11} \\ D_{22} \\ D_{33} \\ 2D_{12} \\ 2D_{23} \\ 2D_{31} \end{Bmatrix}\Bigg|_{t+\theta\Delta t}$$

Convergence is then detected according to the effective stresses of the respective Gauss points in the elements (step S190). The procedure of this embodiment detects convergence upon satisfaction of Equation (86) for all the Gauss points in all the elements. Here 'ε' represents a sufficiently small positive value in Equation (86). In the case of no detection of the convergence, the soil-water coupled analysis program 30 returns to step S150 to calculate the total load increment vector and the total flow increment vector and repeats the subsequent processing of steps S150 to S190.

$$\left|\frac{T_e^{'(n)} - T_e^{'(n-1)}}{T_e^{'(n)}}\right| \leq \varepsilon \quad (86)$$

$$T_e^{'(n)} = \|T^{'(n)}\| = \sqrt{T^{'(n)}\cdot T^{'(n)}}: \quad (87)$$

norm of effective stress tensor $T^{'(n)}$ at Gauss point obtained by n-times iterative computations at time $t = t + \theta\Delta t$ In the case of detection of the convergence at step S190, on the other hand, the soil-water coupled analysis program 30 calculates an acceleration field, a velocity field, coordinates, and various state quantities at a time t=t+Δt and identifies a loading state of each Gauss point (step S200). The acceleration field, the velocity field, and the coordinates at the time t=t+Δt are computed from the total increment vector concerning jerk at the time t=t+θΔt and a total increment vector concerning acceleration, a total increment vector concerning velocity, and a coordinate vector at the time t=t according to Equations (88) to (90) given below. Respective state quantities and their rates at the time t=t+Δt are calculated by Equations (91) and (92) from the state quantities at the time t=t and at the time t=t+θΔt. The loading state of Each Gauss point at the time t=t+Δt is identified based on the respective state quantities at the time t=t+Δt according to Equations (81) and (82).

$$\{\dot{v}^N(\theta\Delta t)^2\}|_{t+\Delta t} = \quad (88)$$

$$\{\dot{v}^N(\theta\Delta t)^2\}|_t + \frac{1}{\theta}\{\ddot{v}^N(\theta\Delta t)^3\}|_t + \frac{1}{2\theta^2}\left[\{\dddot{v}^N(\theta\Delta t)^3\}|_{t+\theta\Delta t} - \{\dddot{v}^N(\theta\Delta t)^3\}|_t\right]$$

$$\{v^N(\theta\Delta t)\}|_{t+\Delta t} = \{v^N(\theta\Delta t)\}|_t + \frac{1}{\theta}\{\dot{v}^N(\theta\Delta t)^2\}|_t + \frac{1}{2\theta^2}\{\ddot{v}^N(\theta\Delta t)^3\}|_t + \qquad (89)$$

$$\frac{1}{6\theta^3}[\{\dddot{v}^N(\theta\Delta t)^3\}|_{t+\theta\Delta t} - \{\dddot{v}^N(\theta\Delta t)^3\}|_t]$$

$$\{x^N\}|_{t+\Delta t} = \qquad (90)$$

$$\{x^N\}|_t + \frac{1}{\theta}\{v^N(\theta\Delta t)\}|_t + \frac{1}{2\theta^2}\{\dot{v}^N(\theta\Delta t)^2\}|_t + \frac{1}{6\theta^3}\{\ddot{v}^N(\theta\Delta t)^3\}|_t +$$

$$\frac{1}{24\theta^4}[\{\dddot{v}^N(\theta\Delta t)^3\}|_{t+\theta\Delta t} - \{\dddot{v}^N(\theta\Delta t)^3\}|_t]$$

$$\dot{A}|_{t+\Delta t}(\theta\Delta t) = 2(A|_{t+\theta\Delta t} - A|_t) - \dot{A}|_t(\theta\Delta t) \qquad (91)$$

$$A|_{t+\Delta t} = A|_t + \frac{1}{2\theta}\{\dot{A}|_{t+\Delta t}(\theta\Delta t) + \dot{A}|_t(\theta\Delta t)\} \qquad (92)$$

$A|_{t+\Delta t}$: state quantity A at time $t=t+\Delta t$ $\dot{A}|_{t+\Delta t}$: rate of state quantity A at time $t=t+\Delta t$ It is then determined whether the current computation flow reaches the number of computation steps input at step S100 (step S210). Upon dissatisfaction of the input number of computation steps, the soil-water coupled analysis program 30 returns to step S130 to estimate the various conditions (for example, effective stress, pore water pressure, structure/overconsolidation, and anisotropy) at the time $t=t+\theta\Delta t$. Upon satisfaction of the input number of computation steps, on the other hand, the soil-water coupled analysis program 30 is terminated after output of the computation results in the form of a specified output file (step S220).

One concrete example of the output file is shown in FIG. 12. In the output file of FIG. 12, data on the 1st line successively show the number of elements, the number of nodes, the number of elements with application of distributed load rate, the number of nodes with application of distributed load rate, the number of nodes per element, the number of nodes×the number of dimensions, the number of nodes per element×the number of dimensions, the specified number of computation steps, the total number of implemented computation steps, the number of dimensions, the number of Gauss points per element, and the number of elastic elements. Data on the 2nd line successively show an analysis condition, a deformation theory, an effective stress rate in adoption of the finite deformation theory, the setting of convergence or non-convergence, a constitutive equation, an output method of state quantity data, a format of output data, and the setting of consideration or non-consideration of self weight. Data on the 3rd to the 11th lines successively show each of node numbers, a type of boundary condition in the x-direction, a value of the boundary condition in the x-direction, a type of boundary condition in the y-direction, and a value of the boundary condition in the y-direction with regard to the corresponding node. Data on the 12th line show the number of nodes requiring output of the reactive force, and data on the 13th line show node numbers requiring output of the reactive force as values including directions at the corresponding nodes. Although being 'omitted' in the illustrated example of FIG. 12, the output file also includes material parameters at respective Gauss points in each element, values of components at each node, a value of pore water pressure in each element, values of effective stress components at respective Gauss points in each element, and a degree of structure. In the output file of FIG. 12, data on the 1st line after the 'omission' show the sequence of an element number and specified (four) relevant elements of the element with regard to the elements 1 to 4. Data on the 2nd line after the 'omission' shows the number of conditions satisfying a fixed length between two nodes. When the number of conditions is not less than 1, its condition number and specification of nodes involved in the condition are shown on a next line inserted immediately below. Data on the 3rd line after the 'omission' shows the number of conditions satisfying a fixed angle between three nodes. Data on the 4th line after the 'omission' show a condition number satisfying the fixed angle between three nodes and specification of (three) nodes involved in the condition. Data on the 5th line after the 'omission' shows the number of conditions satisfying a fixed direction of a relative velocity of two nodes specified by relative position vectors of former two nodes and latter two nodes. Data on the 6th line after the 'omission' show a condition number satisfying the fixed direction of the relative velocity of two nodes and specification of nodes involved in the condition. Data on the 7th line after the 'omission' shows the number of conditions satisfying an equal displacement (velocity). When there is any condition satisfying the equal displacement (velocity), its condition number and specification relating to the condition are shown on a next line inserted immediately below. Data on the 8th line after the 'omission' show the types of soil in the respective elements. Data on the 9th line after the 'omission' successively show the number of input regular waves and the number of input irregular waves. Data on the 10th and 11th lines after the 'omission' regard the regular waves and show a type of regular wave vibration, the number of nodes under influence of the regular wave vibration, the amplitude and the period of the regular wave vibration, and node numbers under influence of the regular wave vibration as values including directions. When there is any input irregular wave, a type of irregular wave vibration, the number of nodes under influence of the irregular wave vibration, and node numbers under influence of the irregular wave vibration as values including directions are shown on next two lines. Data on the last line shows a total time since start of computation.

Figure 13:
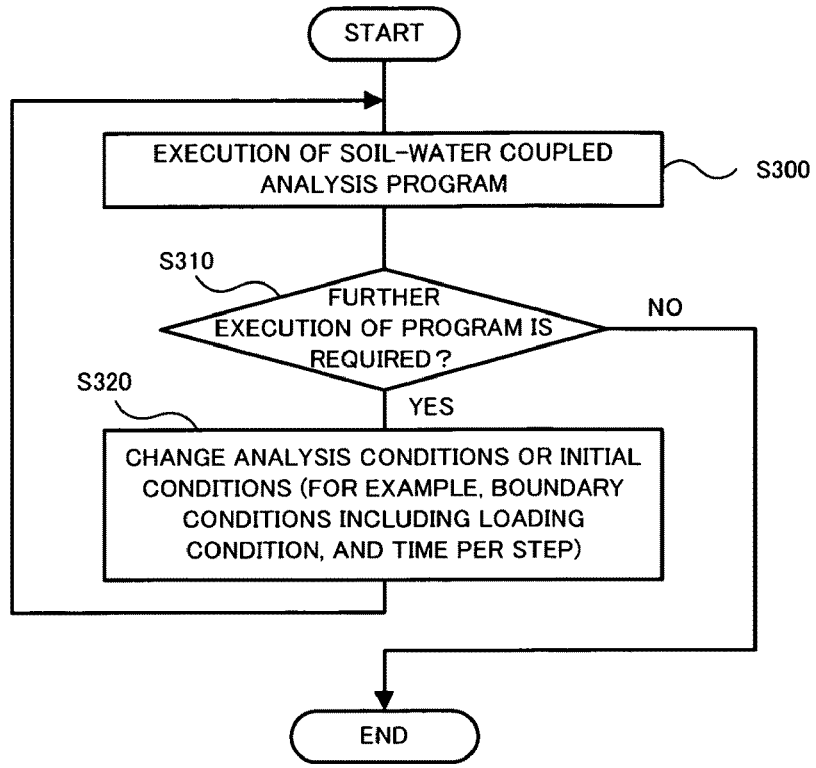
FIG. 13 is a flowchart showing a series of processing upon requirement for repeated execution of the soil-water coupled analysis program with results of the computation set to new analysis conditions or initial conditions.

As described above, the soil-water coupled analysis program 30 of the embodiment inputs multiple different types of soil to be set to the respective elements of the soil foundation. The elasto-plastic deformation behaviors of the soil skeleton are thus estimated in the soil-water coupled field under various loading conditions including dynamic loading conditions and static loading conditions with regard to the naturally-deposited, highly structured and overconsolidated ground or specimen, as well as the artificially made remolded soil. The soil-water coupled analysis program 30 of the embodiment is executed to estimate the deformation behaviors (including bifurcation behavior and post-peak behavior) and self weight consolidation analysis of the specimen, the consolidation settlement and lateral movement behaviors (including 'secondary consolidation' long-term continuous settlement behavior) of soil under loading like road embankment, the soil deformation behaviors in excavation, the liquefaction and liquefaction-induced settlement behaviors under repetitive loading like earthquake, the interaction with an elastic structure (deformation behaviors of the pile draft foundation), and the deformation behaviors of reinforced soil. The soil-water coupled analysis program 30 of the embodiment is also executed to study and investigate the water pumping-induced soil subsidence, the soil bearing capacity, the stability/instability by the groundwater flow, the compacted soil improvement with the cylindrical cavity expansion by sand piles, the soil improvement by improvement of mass permeability, and the stability of an elasto-plastic embankment structure. In the case of such estimations and studies, execution of the soil-water coupled analysis program plural times may be required with the results of the analysis set for new analysis conditions or initial conditions. In this case, as shown in the flowchart of FIG. 13, after execution of the soil-water coupled analysis program (step S300), it is determined whether further execution of the program is required (step S310). Upon requirement for further execution, the soil-water coupled analysis program is executed again (step S300) after change of the analysis conditions or the initial conditions (step S320). Upon no requirement for further execution, the soil-water coupled analysis program is terminated.

Figure 14:
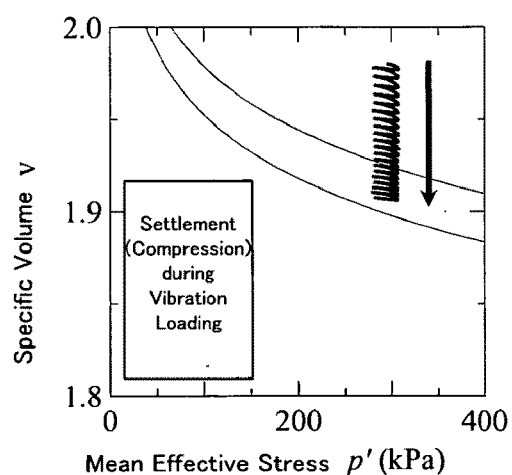
FIG. 14 is a graph showing a computation result under loading of a low-frequency microvibration on a triaxial sand specimen in a drained condition on a boundary.
Figure 15:
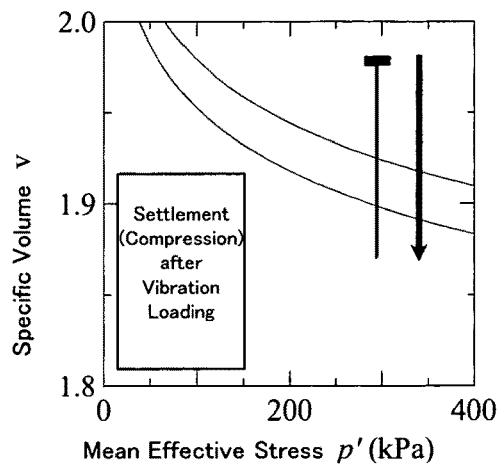
FIG. 15 is a graph showing a computation result under loading of a high-frequency microvibration on the triaxial sand specimen in the drained condition on the boundary.

Some examples of computation are given with regard to the stiffness recovery of the soil skeleton accompanied with compaction and liquefaction-induced settlement. FIG. 14 is a graph showing a computation result under loading of a low-frequency microvibration on a triaxial sand specimen, and FIG. 15 is a graph showing a computation result under loading of a high-frequency microvibration on the triaxial sand specimen. As clearly shown by the comparison between these two graphs, compaction starts in the course of application of low-frequency microvibration load, while liquefaction occurs in the course of application of high-frequency microvibration load and compaction starts after completion of the load application. Under the condition of a fixed cycle rate, application of the high-frequency microvibration load causes the greater compaction. The liquefaction-induced settlement is simulated by first executing the soil-water coupled analysis program under the vibration loading condition in the initial state and subsequently executing the soil-water coupled analysis program under the vibration unloading condition in the computation result set to the new initial state.

Figure 16:
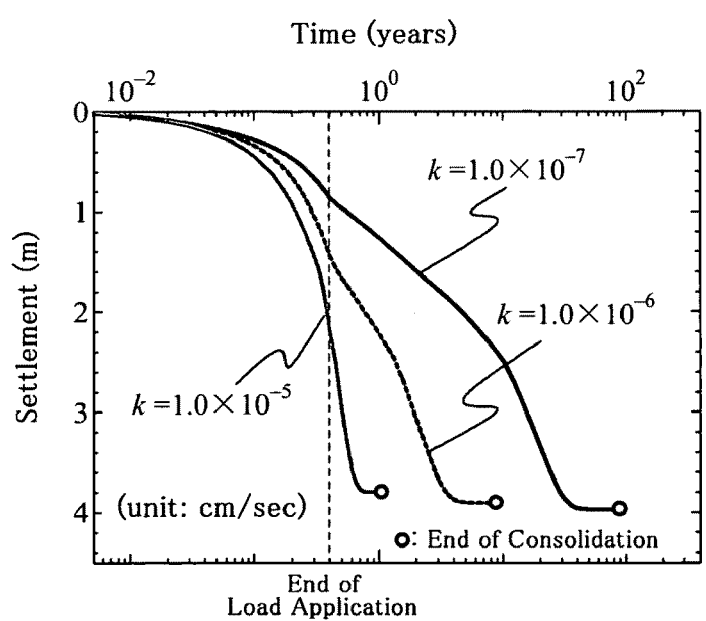
FIG. 16 shows variations in delayed settlement behavior of a naturally deposited clay foundation under embankment loading (long-term continuous settlement behavior) against the improvement in mass permeability (overall water permeability of the soil foundation) by the sand drain method.

As a possible measure against delayed settlement of a naturally deposited clay foundation, FIG. 16 shows variations in delayed settlement behavior of the naturally deposited clay foundation under embankment loading (long-term continuous settlement behavior) against the improvement in mass permeability (overall water permeability of the soil foundation) by the sand drain method. The higher mass permeability 'k' represents the enhanced water permeability. As clearly shown in this graph, the unimproved water permeability leads to duration of settlement over 50 years and gives a greater remaining settlement after completion of embankment loading. The improved water permeability, on the other hand, causes early convergence of settlement and gives a less residual settlement after completion of embankment loading.

As described in detail above, the soil-water coupled analyzer 20 of the embodiment determines the unknown 'jerk field' and the pore water pressure field according to the global tangent stiffness equation (simultaneous linear equations) under the geometric boundary condition with regard to the displacement, the displacement rate, or the acceleration, the mechanical boundary condition with regard to the stress or the stress rate, and the hydraulic boundary conditions with regard to the pore water pressure or the total water head and the flow of pore water. The global tangent stiffness equation is formulated by using the global L matrix, the modified global L matrix, the global H matrix, the global M matrix, and the global K matrix. This allows consideration of the geometric change of the soil foundation and enables large deformation analysis requiring accurate measurement of the volume change rate of soil between deformation to failure or with regard to the behavior after the failure. The soil-water coupled analyzer 20 of the embodiment sets the type of soil for each element of the soil foundation and is thus preferably applicable to computation of mechanical behaviors in a wide range of soil skeleton structure (structure, overconsolidation, anisotropy) including a continuously varying soil structure of sand, intermediate soil to clay, unusual soils like volcanic ash soil, and a layered soil structure of sand, clay, and intermediate soil. In the case of a response having little effect of the acceleration, the global tangent stiffness equation is equal to a global stiffness equation obtained by static analysis. The mechanical behaviors of the soil skeleton are thus computable by both dynamic analysis and static analysis. The soil-water coupled analyzer 20 of the embodiment is applicable to study not only the consolidation deformation behaviors after earthquake-induced liquefaction but the static deformation analysis following the dynamic deformation analysis, such as seismic deformation behaviors during consolidation deformation, and the dynamic deformation analysis following the static deformation analysis.

The soil-water coupled analyzer 20 of the embodiment sets the type of soil for each element of the soil foundation. The possible options of the soil type may be limited. The type of soil may be set for each block of elements, instead of for each element.

The soil-water coupled analyzer 20 of the embodiment accurately calculates the global L matrix, the modified global L matrix, the global H matrix, the global M matrix, and the global K matrix with regard to their respective element matrixes. The calculation may, however, be not strict but approximate.

The soil-water coupled analyzer 20 of the embodiment calculates the global L matrix, the modified global L matrix, the global H matrix, the global M matrix, and the global K matrix and formulates the global tangent stiffness equation (simultaneous linear equations) by using all these matrixes. One possible modification may formulate the global tangent stiffness equation (simultaneous linear equations) by using only part of the global L matrix, the modified global L matrix, the global H matrix, the global M matrix, and the global K matrix. These matrixes are not restrictive but any other suitable matrixes may be used for the same purpose.

The soil-water coupled analyzer 20 of the embodiment adopts the finite element method for deformation analysis of the soil skeleton. The finite element method is, however, not essential, and any other suitable technique may be adopted for deformation analysis of the soil skeleton.

The soil-water coupled analyzer 20 of the embodiment inputs the settings of analysis conditions as shown in the concrete examples of FIGS. 5 and 6. The input analysis conditions include the setting of the computation condition selected among 'plane strain', 'axisymmetric', and 'three-dimensional', the setting of the deformation theory selected between 'small deformation theory' and 'finite deformation theory', the setting of the effective stress rate with objectivity in the finite deformation theory selected between 'Jaumann's rate of Cauchy stress' and 'Green-Naghdi's rate', the setting of convergence or non-convergence, the setting of the constitutive equation selected between 'original Cam-clay model with super-subloading yield surfaces and rotational hardening' and 'modified Cam-clay model with super-subloading yield surfaces and rotational hardening', the setting of state quantity output data selected between 'element average of Gauss points' and 'value of specified Gauss point', the setting of the output data format selected between 'Text' and 'Binary', and the setting of consideration or non-consideration of self weight. The input analysis conditions further include the settings of a current program number, the number of computation steps, the computation time DT per one computation step (sec/step), the number of divisions of excavated load in excavation, the number of divisions of distributed load in application of distributed load, the input file for soil material parameters and initial values, the input file for mesh data, specification of the output file for initial computation conditions used in execution of a next program, specification of the output file for coordinates, specification of the output file for state classification (unloading, loading (plastic compression/expansion, hardening/softening)), specification of the output file for the reactive force, specification of the output file for the pore water pressure, specification of the output file for the mean effective stress p' and the shear stress q, specification of the output file for the degree R of overconsolidation (=1/OCR: OCR represents the overconsolidation ratio), specification of the output file for the degree R* of structure, specification of the output file for the slope of the hardening/softening threshold line, specification of the output file for the plastic volume strain, specification of the output file for initial conditions, specification of the output file for the slope of the plastic compression/expansion threshold line, specification of the output file for the evolution degree of anisotropy, specification of the output file for the elapsed time, and output of file***.dat (preceding output file specifications). The input analysis conditions are, however, not restricted to these parameters. Only part of these parameters may be input as the analysis conditions or any other suitable parameters may be input as the analysis conditions. These analysis conditions may be input in any suitable input format.

The soil-water coupled analyzer 20 of the embodiment inputs the settings of soils as clay, intermediate soil, and sand with regard to the respective elements of the soil foundation as shown in the concrete example of FIG. 7. The input settings of soils include the number of soil types, the number of elastic body types, specification of the plastic measure adopted in the evolution rule of structure, the intercept N of the isotropic normal consolidation line of remolded soil, the critical state constant M, the compression index $\lambda$, the swelling index $\kappa$, the Poisson's ratio $\nu$, the coefficient of permeability k, the specific gravity Gs of soil particles, the initial lateral pressure coefficient K0, the initial degree R0 of overconsolidation, the initial degree R*0 of structure, the normal consolidation index m, the U* shape, the structural degradation index a, the structural degradation index b, the structural degradation index c, the rotational hardening index br, the rotational hardening limit surface mb, the initial degree of anisotropy, the initial void ratio, the height of soil foundation/specimen, the water surface level, the initial overburden pressure on the surface of the soil foundation, the initial consolidation pressure of the specimen, the cell pressure (tensile: positive), and settings of the unit system (time, force, and length). The input settings of soils are, however, not restricted to these parameters. Only part of these parameters may be input as the settings of soils or any other suitable parameters may be input as the settings of soils. These settings of soils may be input in any suitable input format.

The soil-water coupled analyzer 20 of the embodiment inputs the settings of the solid soil model as shown in the concrete example of FIG. 8. The input settings of the solid soil model in the file of FIG. 8 include the number of elements, the number of nodes, and the number of elements with application of distributed load rate in the solid soil model, the number of nodes per element, the number of computation steps, and the number of elastic elements on the $1^{st}$ line, each of node numbers and the type of boundary condition in the x-direction, the value of the boundary condition in the x-direction, the type of boundary condition in the y-direction, and the value of the boundary condition in the y-direction with regard to the corresponding node on the $2^{nd}$ to the $10^{th}$ lines, each of element numbers and the global node numbers mapped to the local node numbers with regard to the corresponding element on the $11^{th}$ to the $14^{th}$ lines, each of node numbers and the coordinate in the x-direction and the coordinate in the y-direction of the corresponding node on the $15^{th}$ to the $23^{rd}$ lines, the number of nodes requiring output of the reactive force and their node numbers on the $24^{th}$ and $25^{th}$ lines. The input settings of the solid soil model in the file of FIG. 8 also include element numbers with application of distributed load rate and the side of application (internode of application), the value of the distributed load rate of its left node in the x-direction, the value of the distributed load rate in its left node in the y-direction, the value of the distributed load rate of its right node in the x-direction, and the value of the distributed load rate of its right node in the y-direction with regard to the corresponding element on the $26^{th}$ and $27^{th}$ lines, and each of element numbers and the element number adjacent to the internode 1 of the corresponding element, the element number adjacent to the internode 2 of the corresponding element, the element number adjacent to the internode 3 of the corresponding element, the element number adjacent to the internode 4 of the corresponding element, and the soil type of the corresponding element on the $28^{th}$ to the $31^{st}$ lines. The input settings of the solid soil model in the file of FIG. 8 further include the number of conditions satisfying the fixed length between two nodes on the $32^{nd}$ line, the number of conditions satisfying the fixed angle between three nodes on the $33^{rd}$ line, the number of conditions satisfying the fixed direction of the relative velocity of two nodes specified by relative position vectors of former two nodes and latter two nodes on the $35^{th}$ line, the condition number satisfying the fixed direction of the relative velocity of two nodes and specification of nodes involved in the condition on the $36^{th}$ line, the number of conditions satisfying the equal displacement (velocity) on the $37^{th}$ line, the number of regular waves input into the model and the number of irregular waves input into the model on the $38^{th}$ line, the type of regular wave vibration, the number of nodes under influence of the regular wave vibration, and the amplitude and the period of the regular wave vibration on the $39^{th}$ line, and specification of nodes under influence of the regular wave vibration on the $40^{th}$ line. The input settings of the solid soil model are, however, not restricted to these parameters. Only part of these parameters may be input as the settings of the solid soil model or any other suitable parameters may be input as the settings of the soil soil model. These settings of the solid soil model may be input in any suitable input format.

The soil-water coupled analyzer 20 of the embodiment performs the computations with the pore water set to an uncompressible fluid. The computations may alternatively be performed with the pore water set to a compressible fluid. In the latter case, the global tangent stiffness equation (Equation (63)) is solved with some modification using a pore ratio e estimated as the value of the element i at the time $t=t+\theta\Delta t$ in the course of convergence calculation and a density of pore water given by Equation (93). In the coefficient matrix on the left side of Equation (63), (two) transposed L terms of the global L matrix (global volume change rate matrix) are replaced by transposed sums of the corresponding L terms and a global Lc matrix (global pore water compressibility matrix) given by Equation (94).

$$\rho_w = \rho_{w0} \exp\left(\frac{u - u_{w0}}{K_f}\right) \quad (93)$$

$\rho_{w0}$: density of pore water under reference water pressure $u_{w0}$
$K_f$: bulk modulus of elasticity of pore water $$L_c = \begin{bmatrix} L_c^{e1} \\ L_c^{e2} \\ \vdots \\ L_c^{ei} \\ \vdots \\ L_c^{e(NE-1)} \\ L_c^{eNE} \end{bmatrix} : \quad (94)$$

global Lc matrix (global pore water compressibility matrix)

$$L_c^{ei} = -\int_{ve^i} \frac{\rho_w}{K_f} \frac{e}{1+e} [N]^T ([N]\{\dot{v}^N\} - \{b\}) dv: \quad (95)$$

element Lc matrix (element water compressibility matrix) of element $i$

In the coefficient matrix on the left side of Equation (63), the global H matrix (Equation (16)) is replaced by a modified global H matrix given by Equation (96). Equation (98) is added to the lower term on the right side of Equation (63).

$$H_c = \begin{bmatrix} H_c^{e1} \\ H_c^{e2} \\ \vdots \\ H_c^{ei} \\ \vdots \\ H_c^{e(NE-1)} \\ H_c^{eNE} \end{bmatrix} : \quad (96)$$

modified global $H$ matrix (modified global water permeability matrix)

$$H_c^{ei} = \left[\alpha_1^{ei} \ \ldots \ \alpha_m^{ei} \ \ldots \ \alpha_s^{ei}\left(-\sum_{m=1}^{s}\alpha_m^{ei} - \frac{2}{K_f}\frac{e}{1+e}\frac{1}{\theta\Delta t}\right)\right] : \quad (97)$$

element Hc matrix (modified element water permeability matrix) of element $i$

-continued $$\{\hat{f}_c(\theta\Delta t)\}\big|_t = \begin{Bmatrix} -2\frac{1}{K_f}\frac{e}{1+e}\left(u^1 + \frac{1}{2}\dot{u}^1(\theta\Delta t)\right) \\ -2\frac{1}{K_f}\frac{e}{1+e}\left(u^2 + \frac{1}{2}\dot{u}^2(\theta\Delta t)\right) \\ \vdots \\ -2\frac{1}{K_f}\frac{e}{1+e}\left(u^i + \frac{1}{2}\dot{u}^i(\theta\Delta t)\right) \\ \vdots \\ -2\frac{1}{K_f}\frac{e}{1+e}\left(u^{(NE-1)} + \frac{1}{2}\dot{u}^{(NE-1)}(\theta\Delta t)\right) \\ -2\frac{1}{K_f}\frac{e}{1+e}\left(u^{NE} + \frac{1}{2}\dot{u}^{NE}(\theta\Delta t)\right) \end{Bmatrix}_t \quad (98)$$

Figure 17:
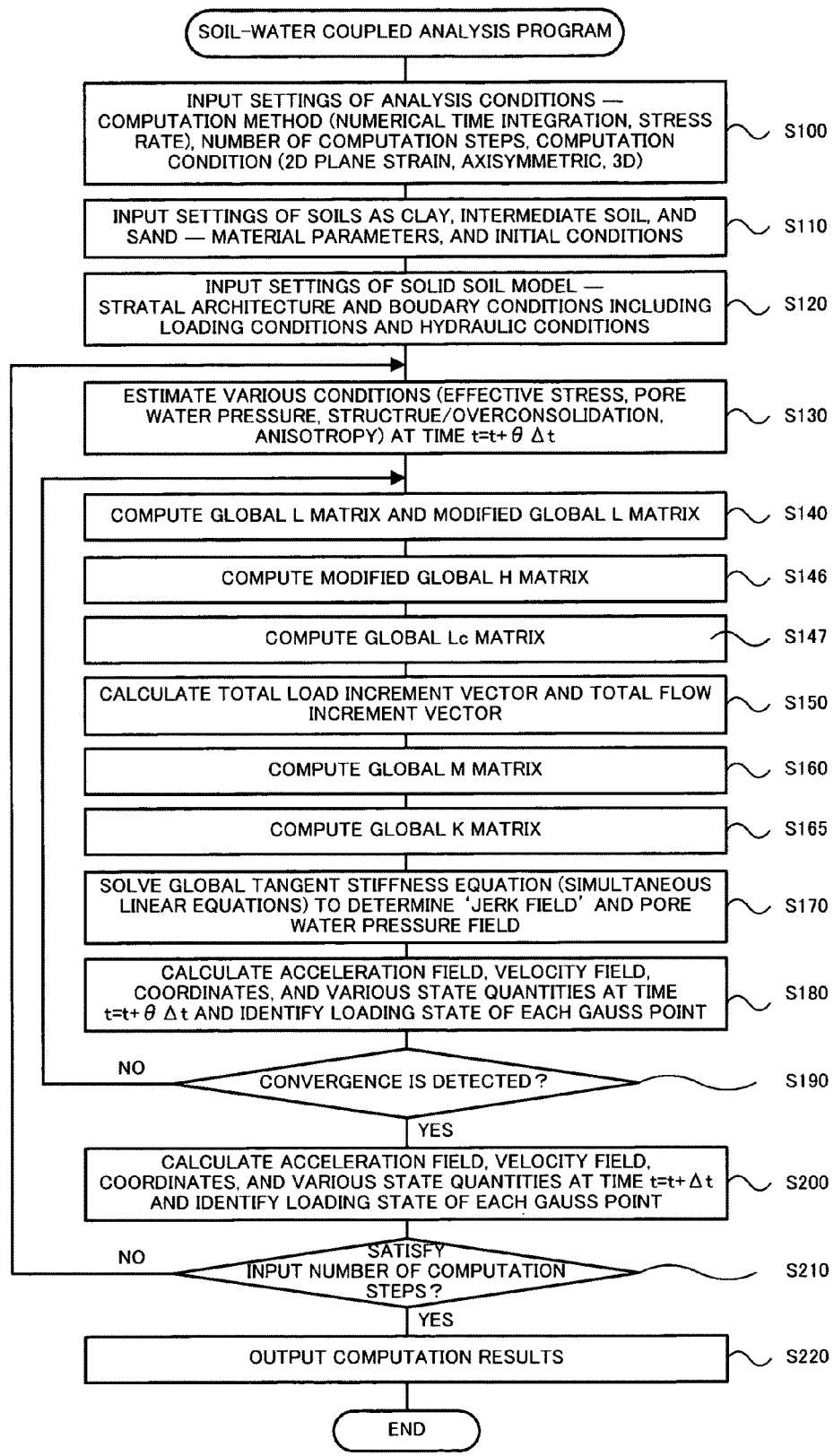
FIG. 17 is a flowchart showing a modified series of processing according to the soil-water coupled analysis program 30 with pore water set to a compressible fluid.

In this modification, the soil-water coupled analysis program 30 adopts a modified flow shown in the flowchart of FIG. 17, in place of the Tamura/Christian model of the algorithm shown in the flowchart of FIG. 2. The modified flow of FIG. 17 computes the modified global H matrix by Equation (96) (step S146) and the global pore water compressibility matrix (global Lc matrix) by Equation (94) (step S147), instead of the computation of the global H matrix at step S145 in the flow of FIG. 2. The modified flow also calculates Equation (98) in the computation of the total load increment vector and the total flow increment vector at step S150. The density of pore water calculated from the water pressure at the element center according to Equation (93) is substituted into the relevant terms (for example, Equations (35) and (36)). The iterative loop to detection of the convergence at step S190 is from step S140 to step S180 in this modified flow. It is desirable to add a coefficient of volume compressibility Kf of pore water to the input settings of soils shown as the concrete example of FIG. 7. The coefficient of permeability may be varied corresponding to the void ratio.

Figure 18:
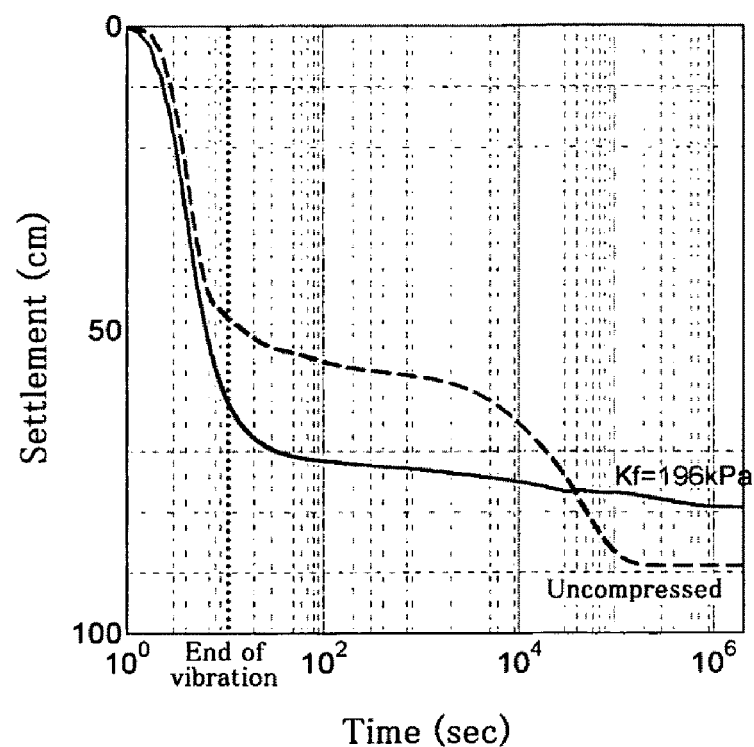
FIG. 18 shows time-settlement curves after a start of seismic vibration immediately below embankment as an example of computation with consideration of the compressibility of pore water.

FIG. 18 shows time-settlement curves after a start of earthquake motion immediately below embankment as an example of computation with consideration of the compressibility of pore water. The 'earthquake motion' of about 100 gal at the maximum is given at the cycle of approximately 1 second from the bottom of a loose sand foundation (layered thickness of 20 m, embankment height of 4 m) having the varying compressibility of pore water only in a lower area of the embankment loading. The time-settlement curve for the compressible pore water has a significant compaction in the lower area of the embankment during the earthquake. The time-settlement curve for the compressible pore water has the greater depth of settlement in the initial stage after the end of the earthquake but eventually the less depth of settlement with elapse of time, compared with the time-settlement curve for the uncompressed pore water. The general conditions of the soil foundation are expected to change with the variation in compressibility of pore water in the lower area of the loading embankment. In this example of computation, the density $\rho_{w0}$ of compressible pore water at a reference water pressure $u_{w0}$ is varied to prevent the potential change of the conditions of the soil foundation.

The soil-water coupled analyzer 20 of the embodiment may execute the soil-water coupled analysis program plural times with the results of the analysis set for new analysis conditions or initial conditions. The iterative execution of the soil-water coupled analysis program may be limited to a preset number of times, or execution of the soil-water coupled analysis program may be allowed only once.

The soil-water coupled analyzer 20 of the embodiment computes the element K matrix according to Equation (39) as the sum of the first term representing the tangent stiffness of giving the mechanical behaviors of the specified soil materials (for example, sand and clay), the second term representing the contribution of the geometric time change of the soil to the tangent stiffness, the third term representing the contribution to the tangent stiffness under application of a significant acceleration to the soil skeleton, for example, under application of an impact load, and the fourth term representing the contribution to the tangent stiffness under application of a body force. According to the analysis conditions, part of these terms may be omitted from the computation of the element K matrix.

The soil-water coupled analyzer 20 of the embodiment is applicable to the analyses for any of the two-dimensional plane strain condition, the axisymmetric condition, and the three-dimensional condition. The soil-water coupled analyzer may be designed to allow the analysis only for the two-dimensional plane strain condition or the analyses only for the two-dimensional plane strain condition and the axisymmetric condition.

The soil-water coupled analyzer 20 of the embodiment is adopted to estimate the deformation behaviors (including bifurcation behavior and post-peak behavior) and self weight consolidation analysis of the specimen, the consolidation settlement and lateral movement behaviors (including 'secondary consolidation' long-term continuous settlement behavior) of soil under loading like road embankment, the soil deformation behaviors in excavation, the liquefaction and liquefaction-induced settlement behaviors under repetitive loading like earthquake, the interaction with an elastic structure (deformation behaviors of the piled raft foundation), and the deformation behaviors of reinforced soil. The soil-water coupled analyzer 20 of the embodiment is also adopted to study and investigate the water pumping-induced soil subsidence, the soil bearing capacity, the stability/instability by the groundwater flow, the compacted soil improvement with the cylindrical cavity expansion by sand piles, the soil improvement by improvement of mass permeability, and the stability of an elasto-plastic embankment structure. In the case of such estimations and studies, execution of the soil-water coupled analysis program plural times may be required with the results of the analysis set for new analysis conditions or initial conditions. The soil-water coupled analyzer 20 may be adopted for estimation or investigation of only part or only one of these behaviors and problems.

The embodiment regards the soil-water coupled analyzer 20 with the soil-water coupled analysis program 30 installed therein. The technique of the invention may be attained by the soil-water coupled analysis program 30 or by the computation module 34 of the soil-water coupled analysis program 30.

The embodiment and its modified examples discussed above are to be considered in all aspects as illustrative and not restrictive. There may be many modifications, changes, and alterations without departing from the scope or spirit of the main characteristics of the present invention.

The present application claims priority from Japanese patent application No. 2005-301415 filed on Oct. 17, 2005, the entire contents of which are hereby incorporated by reference into this application.

INDUSTRIAL APPLICABILITY

The technique of the invention is preferably applicable to the manufacturing industries utilizing the soil-water coupled analyzer.

DESCRIPTION OF NOTATIONS $l_m$: relative position vector from center of gravity of element i to center of gravity of element m h: total water head at center of gravity of element i $h_m$: total water head at center of gravity of element m $h_c$: total water head at intersection of $l_i$ and interface between element i and element m $v'^m_i$: flow rate vector of pore water in element i toward element m $v'^m_m$: flow rate vector of pore water in element m from element i $r_a, r_b$: distance from axis of rotational symmetry to two nodes at interface between element i and element m

The invention claimed is:

1. A soil-water coupled analyzer comprising:
a processor that:
inputs data on conditions of a soil skeleton and data on external forces;
performs deformation analysis of the soil skeleton, wherein the deformation analysis formulates simultaneous motion equations of rate type with respect to a pore water pressure and a velocity of the solid skeleton including a jerk term of a second order derivative term on a time of a velocity vector of the soil skeleton, based on the input data on the conditions of the soil skeleton and the input data on the external forces, and integrates the formulated simultaneous motion equations as needed under a given geometric boundary condition with the regard to any of the displacements, a displacement rate, and an acceleration, a given dynamic boundary condition with regard to either of a stress and a stress rate, and given hydraulic boundary conditions with regard to either of the pore water pressure and a total water head and a flow of pore water, so as to obtain time history responses of a velocity field and pore water pressure field; and
outputs the obtained time history responses.

2. The soil-water coupled analyzer in accordance with claim 1, wherein the analysis module calculates multiple terms based on the input data on the conditions of the solid skeleton and the input data on the external forces and formulates the simultaneous motion equations of rate type using the multiple calculated terms, where the multiple terms include at least one of the first term regarding a volume change rate of the soil skeleton over time, a second term regarding a water permeability of soil, a third term regarding a mass, and a fourth term regarding a tangent stiffness of the soil skeleton.

3. The soil-water coupled analyzer in accordance with claim 2, wherein the analysis module formulates the simultaneous motion equations of rate type using all of the first term, the second term, the third term, and the fourth term.

4. The soil-water coupled analyzer in accordance with claim 1, wherein the analysis module adopts a numerical analysis technique, such as a finite element method or a difference method, to formulate the simultaneous motion equations of rate type.

5. The soil-water coupled analyzer in accordance with claim 1, wherein the data on the conditions of the soil skeleton include data on properties of multiple elements constituting the soil skeleton and data on relations between adjacent elements.

6. The soil-water coupled analyzer in accordance with claim 5, wherein the data on the properties of the multiple elements include data on properties of soils.

7. The soil-water coupled analyzer in accordance with claim 1, wherein the data on the external forces include data on a load and a displacement applied to a soil-water coupled system.

8. The soil-water coupled analyzer in accordance with claim 1, wherein the data on the external forces include data on a vibration applied to a soil-water coupled system.

9. The soil-water coupled analyzer in accordance with claim 8, wherein the analysis module performs the deformation analysis plural times with setting a result of a current cycle of the analysis prior to the change of the data on the external forces to an initial state of the data on the conditions of the soil skeleton for a next cycle of the analysis.

10. The soil-water coupled analyzer in accordance with claim 1, wherein the analysis module performs the deformation analysis plural times with changing the data on the external forces.

11. A non-transitory computer readable medium comprising programming for execution by a processor, the programming when executed, performing a soil-water coupled analysis method, the method comprising:

performing deformation analysis of a soil skeleton, wherein the deformation analysis:

formulates simultaneous motion equations of rate type with respect to a pore water pressure and a velocity of the soil skeleton including a jerk term of a second order derivative term on a time of a velocity vector of the soil skeleton, based on data on conditions of the soil skeleton and data on external forces, and integrates the formulated simultaneous motion equations as needed under a given geometric boundary condition with regard to any of a displacement, a displacement rate, and an acceleration, a given dynamic boundary condition with regard to either of a stress and a stress rate, and given hydraulic boundary conditions with regard to either of the pore water pressure and a total water head and a flow of pore water, so as to obtain time history responses of a velocity field and a pore water pressure field.

12. The computer readable medium in accordance with claim 11, wherein the soil-water coupled analysis method calculates multiple terms based on the data on the conditions of the soil skeleton and the data on the external forces and formulates the simultaneous motion equations of rate type using the multiple calculated terms, where the multiple terms include at least one of a first term regarding a volume change rate of the soil skeleton over time, a second term regarding a water permeability of soil, a third term regarding a mass, and a fourth term regarding a tangent stiffness of the soil skeleton.

* * * * *